(12) United States Patent
Tykocinski et al.

(10) Patent No.: US 8,039,437 B2
(45) Date of Patent: Oct. 18, 2011

(54) FN14/TRAIL FUSION PROTEINS

(75) Inventors: Mark L. Tykocinski, Merion Station, PA (US); Marjaneh Razmara, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/494,680

(22) Filed: Jun. 30, 2009

(65) Prior Publication Data

US 2010/0048478 A1 Feb. 25, 2010

Related U.S. Application Data

(60) Provisional application No. 61/133,532, filed on Jun. 30, 2008.

(51) Int. Cl.
*A61K 38/16* (2006.01)
*C07K 14/715* (2006.01)
*C07K 14/52* (2006.01)
*C12N 15/00* (2006.01)

(52) U.S. Cl. ............... 514/12.2; 514/18.9; 514/21.3; 514/21.2; 435/69.7; 530/300; 530/350; 530/351

(58) Field of Classification Search ............. None
See application file for complete search history.

(56) References Cited

U.S. PATENT DOCUMENTS

| | | | |
|---|---|---|---|
| 4,892,538 | A | 1/1990 | Aebischer et al. |
| 5,283,187 | A | 2/1994 | Aebischer et al. |
| 7,208,151 | B2 | 4/2007 | Browning et al. |
| 7,285,522 | B2 | 10/2007 | van Buskirk |
| 7,378,089 | B2 | 5/2008 | Fathman |

FOREIGN PATENT DOCUMENTS

| | | |
|---|---|---|
| WO | WO 93/25673 | 12/1993 |
| WO | WO 96/07321 | 3/1996 |
| WO | WO 01/45730 A2 | 6/2001 |
| WO | WO 03/086311 A2 | 10/2003 |

OTHER PUBLICATIONS

Nakayama et al., Involvement of TWEAK in interferon gamma-stimulated monocyte cytotoxicity, J. Exp. Med. 192(9):1373-1379, Nov. 6, 2000.*
WO 2010005519 A1 srch rpt, Jan. 2010, World Intellect, Razmara M et al.*
Razmara, M. et al, Fn14-TRIAL, a Chimeric Intercellular Signal Exchanger, Attenuates Experimental Autoimmune Encephalomyelitis, AJ Pathology, vol. 174, No. 2, Feb. 2009, pp. 460-474.
Hemmer, B. et al, Immunopathogenesis and immunotherapy of multiple sclerosis, Nature Clinical Practice Neurology, Apr. 2006, vol. 2, No. 4, 201-211.
Mackay F. et al., TNF ligands and receptors in autoimmunity: an update, Curr Opin Immunol 2002, 14:783-790.
Watts, T.H., TNF/TNFR Family Members in Costimulation of T Cell Responses, Annu. Rev. Immunol. 2005, 23:23-68.
Aktas O, et al., Death Ligands and Autoimmune Demyelination, The Neuroscientist, vol. 12, No. 4, 2006, 305-316.
Burkly L.C., et al., TWEAKing tissue remodeling by a multifunctional cytokine: Role of TWEAK/Fn14 pathway in health and disease, Cytokine 40 (2007) 1-16.
Winkles J.A., The TWEAK-Fn14 cytokine-receptor axis: discovery, biology and therapeutic targeting, Nature Reviews, Drug Discovery, vol. 7, May 2008, 411-425.
Lamhamedi-Cherradi S.E., Critical Roles of Tumor Necrosis Factor-Related Apoptosis-Inducing Ligand in Type 1 Diabetes, Diabetes, vol. 52, Sep. 2003,2274-2278.
Cretney E, TNF-related apoptosis-inducing ligand (TRAIL)/Apo2L suppresses experimental autoimmune encephalomyelitis in mice, Immunology and Cell Biology (2005) vol. 83, 511-519.
Hirata S., Prevention of experimental autoimmune encephalomyelitis by transfer of embryonic stem cell-derived dendritic cells . . . J Immunology 2005, 174:1888-1897.
Wandinger K.P., TNF-related apoptosis inducing ligand (TRAIL) as a potential response marker for interferon-beta treatment in multiple sclerosis, Lancet, 2003, 361:2036-2043.
Huang J.H. et al, CTLA-4-Fas ligand functions as a trans signal converter protein in bridging antigen-presenting cells and T cells, Int'l Immunol vol. 13, No. 4, 2001, 529-539.
Elhalel M.D. et al., CTLA-4. FasL induces alloantigen-specific hyporesponsiveness, J Immunol 2003, 170:5842-5850.
Dranitzki-Elhalel M. et al, CTLA-4.FasL inhibits allogeneic responses in vivo, Cellular Immunol, vol. 239 (2006), 129-135.
Orbach A. et al, CTLA-4: FasL induces early apoptosis of activated T cells by interfering with anti-apoptotic signals, J Immunol 2007, 179:7287-7294.
Brunschwig E.B. et al, Glycosylphosphatidylinositol-modified murine B7-1 and B7-2 retain costimulator function, J Immunol 1995, 155:5498-5505.
Liu F. et al, Hydrodynamics-based transfection in animals by systemic administration of plasmid DNA, Gene Therapy (1999), vol. 6, 1258-1266.
Prasad R et al., 5-aminoimidazole-4-carboxamide-1-beta-4-ribofuranoside attenuates experimental autoimmune encephalomyelitis . . . , J Neurosci Research, 2006, 84:614-625.
Hilliard B et al., Experimental autoimmune encephalomyelitis in NF-kappa B-deficient mice:roles of NF-kappa B in the activation . . . , J Immunol 1999, 163:2937-2943.
Hymowitz S.G. et al., Triggering cell death: the crystal structure of Apo2L/TRAIL in a complex with death receptor 5, Molecular Cell, vol. 4, Oct. 1999, 563-571.

(Continued)

*Primary Examiner* — Lorraine Spector
*Assistant Examiner* — Claire Kaufman
(74) *Attorney, Agent, or Firm* — Riverside Law LLP

(57) ABSTRACT

Fusion proteins which act on the TWEAK and TRAIL signaling axes are provided. The proteins are useful in the treatment or amelioration of autoimmune diseases, particularly multiple sclerosis, as well as other diseases such as alloimmune diseases and cancer.

9 Claims, 16 Drawing Sheets

OTHER PUBLICATIONS

Marti-Renom M.A. et al, Comparative protein structure modeling of genes and genomes, Annu Rev Biophys Biomol Struct 2000, 29:291-325.
Isaacs J.D. et al, Therapy with monoclonal antibodies. II. The contribution of Fc gamma receptor binding and the influence of C(H)1 and C(H)3 . . . , J Immunol 1998, 161:3862-3869.
Hymowitz S.G. et al., Structures of APRIL-Receptor Complexes . . . , J Biol Chem, vol. 280, No. 8, Feb. 2005, 7218-7227.
Swaminathan P, Molecular structure, conformational analysis, and structure-activity studies of Dendrotoxin and its homologues . . . , J Med Chem 1996, vol. 39, 2141-2155.
Maecker H. et al., TWEAK attenuates the transition from innate to adaptive immunity, Cell, Dec. 2005, 123:931-944.
Saas P. et al., TWEAK stimulation of astrocytes and the proinflammatory consequences, GLIA 2000, 32:102-107.
Harada N. et al., Pro-inflammatory effect of TWEAK/Fn14 interaction on human umbilical vein endothelial cells, Biochem Biophys Res Commun, vol. 299 (2002), 488-493.
Chicheportiche Y et al., Proinflammatory activity of TWEAK on human dermal fibroblasts and synoviocytes . . . , Arthritis Res 2002, 4:126-133.
Campbell S et al., Proinflammatory effects of TWEAK/Fn14 interactions in glomerular mesangial cells, J Immunol 2006, 176:1889-1898.
Xu H. et al., TWEAK/Fn14 interaction stimulates human bronchial epithelial cells to produce IL-8 and GM-CSF, Biochem Biophys Res Commun, vol. 318 (2004), 422-427.
Ando T et al, TWEAK/Fn14 interaction regulates RANTES production, BMP-2-induced differentiation, and RANKL expression in mouse osteoblastic . . . , Arthritis Res Ther 2006, 8:R146.
Polavarapu R, Tumor necrosis factor-like weak inducer of apoptosis increases the permeability of the neurovascular unit . . . , J Neurosci, Nov. 2005, 25(44):10094-10100.
Jakubowski A. et al, Dual role for TWEAK in angiogenic regulation, J Cell Sci 2002, vol. 115, 267-274.
Kirk S.L. et al., VEGF and vascular changes in chronic neuroinflammation, J Autoimmun 2003, vol. 21, 353-363.
Desplat-Jego S. et al., TWEAK is expressed by glial cells, induces astrocyte proliferation and increases EAE severity, J Neuroimmunolgy 2002, vol. 133, 116-123.
Potrovita I. et al, Tumor necrosis factor-like weak inducer of apoptosis-induced neurodegeneration, J Neurosci, Sep. 2004, 24(38):8237-8244.
Mueller AM, Targeting fibroblast growth factor-inducible-14 signaling protects from chronic relapsing experimental autoimmune encephalomyelitis, J Neuroimmunol 2005, 159:55-65.
Ren X. et al, Involvement of cellular death in TRAIL/DR5-dependent suppression induced by CD4(+)CD25(+) regulatory T cells, Cell Death Differ, 2007, vol. 14, 2076-2084.
Hilliard B et al., Roles of TNF-related apoptosis-inducing ligand in experimental autoimmune encephalomyelitis, J Immunol 2001, 166:1314-1319.
Gold R. et al., Understanding pathogenesis and therapy of multiple sclerosis via animal models . . . , Brain 2006, vol. 129, 1953-1971.
Tykocinski, M.L. et al, New designs for cancer vaccine and artificial veto cells: an emerging palette of protein paints, Immunol Res 2003, 27/2-3:565-574.
Jin Y et al, Simultaneous stimulation of Fas-mediated apoptosis and blockade of costimulation prevent autoimmune diabetes in mice . . . , Gene Ther 2004, vol. 11, 982-991.
Vince J.E. et al, TWEAK shall inherit the earth, Cell Death Differ 2006, vol. 13, 1842-1844.
Cretney E. et al., TNF-related apoptosis-inducing ligand as a therapeutic agent in autoimmunity and cancer, Immunol Cell Biol 2006, vol. 84, 87-98.
Desplat-Jego S. et al., Anti-TWEAK monoclonal antibodies reduce immune cell infiltration in the central nervous system . . . , Clin Immunol 2005, vol. 117, 15-23.
Kim Sh, TWEAK can induce pro-inflammatory cytokines and matrix metalloproteinase-9 in macrophages, Circulation J, Apr. 2004, 68, 396-399.
Lamhamedi-Cherradi S.E. et al., Defective thymocyte apoptosis and accelerated autoimmune diseases in TRAIL-/- mice, Nat Immunol, Mar. 2003, vol. 4. No. 3, 255-260.
Song K et al, Tumor necrosis factor-related apoptosis-inducing ligand (TRAIL) is an inhibitor of autoimmune inflammation & cell cycle progression, J Exp Med 2000 191:1095-1104.
Mi Q.S. et al, Blockade of tumor necrosis factor-related apoptosis-inducing ligand exacerbates type 1 diabetes in NOD mice, Diabetes, Aug. 2003, vol. 52, 1967-1975.
Kayagaki N. et al., Suppression of antibody production by TNF-related apoptosis-inducing ligand (TRAIL), Cell Immunol, 2002, vol. 219, 82-91.
Hayakawa Y. et al., NK cell TRAIL eliminates immature dendritic cells in vivo and limits dendritic cell vaccination efficacy, J Immunol, 2004, vol. 172, 123-129.
Janssen E.M. et al., CD4+ T-cell help controls CD8+ T-cell memory via TRAIL-mediated activation-induced cell death, Nature, Mar. 2005, vol. 434, 88-93.
You R.I. et al., Apoptosis of dendritic cells induced by decoy receptor 3 (DcR3), Blood 2008, vol. 111, 1480-1488.
Smyth M.J. et al., Nature's TRAIL—on a path to cancer immunotherapy, Immunity , vol. 18, Jan. 2003, 1-6.
Kaplan M.J. et al, TRAIL (Apo2 ligand) and TWEAK (Apo3 ligand) mediate CD4+ T cell killing of antigen-presenting macrophages, J Immunol, 2000, vol. 164, 2897-2904.
Renshaw S.A. et al., Acceleration of human neutrophil apoptosis by TRAIL, J Immunol, 2003, vol. 170, 1027-1033.
Lunemann J.D. et al., Death ligand TRAIL induces no apoptosis but inhibits activation of human (auto)antigen-specific T cells, J Immunol, 2002, vol. 168, 4881-4888.
Zhang X.R. et al., Reciprocal expression of TRAIL and CD95L in Th1 and Th2 cells: role of apoptosis in T helper subset differentiation, Cell Death Differ, 2003, vol. 10, 203-210.
Hirata S. et al., Involvement of regulatory T cells in the experimental autoimmune encephalomyelitis-preventive effect of dendritic cells . . . , J Immunol, 2007, vol. 178, 918-925.
Nitsch R. et al., Direct impact of T cells on neurons revealed by two-photon microscopy in living brain tissue, J Neurosci, Mar. 2004, 24(10):2458-2464.
Kennedy K.J. et al, Acute and relapsing experimental autoimmune encephalomyelitis are regulated by differential expression of the CC . . . , J Neuroimmunol 1998, 92:98-108.
Aktas O. et al., Neuronal damage in autoimmune neuroinflammation mediated by the death ligand TRAIL, Neuron, vol. 46, May 2005, 421-432.
Nitsch R. et al., Human brain-cell death induced by tumour-necrosis-factor-related apoptosis-inducing ligand (TRAIL), Lancet, Sep. 2000, vol. 356, 827-828.
Matysiak M. et al., TRAIL induces death of human oligodendrocytes isolated from adult brain, Brain 2002, vol. 125, 2469-2480.
Cantarella G. et al, TRAIL inhibits angiogenesis stimulated by VEGF expression in human glioblastoma cells, British J Cancer, 2006, vol. 94, 1428-1435.
Secchiero P. et al., TRAIL counteracts the proadhesive activity of inflammatory cytokines in endothelial cells by down-modulating CCL8 and CXCL10 . . . Blood 2005, 105:3413-3419.
Perper S.J. et al., TWEAK is a novel arthritogenic mediator, J Immunol, 2006, vol. 177, 2610-2620.
Kamata K. et al., Involvement of TNF-like weak inducer of apoptosis in the pathogenesis of collagen-induced arthritis, J Immunol ,2006, vol. 177, 6433-6439.
Zhao Z et., TWEAK/Fn14 interactions are instrumental in the pathogenesis of nephritis in the chronic graft-versus-host model of systemic lupus . . . , J Immunol 2007,179:7949-7958.
Tanabe K. et al., Fibroblast growth factor-inducible-14 is induced in axotomized neurons and promotes neurite outgrowth, J Neurosci, Oct. 2003, 23(29):9675-9686.
Bover L.C. et al., A previously unrecognized protein-protein interaction between TWEAK and CD163: potential biological implications, J Immunol 2007, 178:8183-8194.
Stromnes I.M. et al., Active induction of experimental allergic encephalomyelitis, Nature Protocols, 2006, vol. 1, No. 4, 1810-1819.

Sospedra M. et al., Immunology of Multiple Sclerosis, Annu Rev Immunol 2005, 23:683-747.

Nakayama M. et al., Characterization of murine TWEAK and its receptor (Fn14) by monoclonal antibodies, Biochem Biophys Res Commun 2003, 306:819-825.

Hilliard B. et al., Roles of TNF-related apoptosis-inducing ligand in experimental autoimmune encephalomyelitis, J Immunol, 2001, 166:1314-1.

Zamvil S.S. et al., The T lymphocyte in experimental allergic encephalomyelitis, Annu Rev Immunol, 1990, 8:579-621.

Mahad D.J. et al., The role of MCP-1 (CCL2) and CCR2 in multiple sclerosis and experimental autoimmune encephalomyelitis (EAE), Semin Immunol, 2003, 15:23-32.

Hofmann N. et al., Increased expression of ICAM-1, VCAM-1, MCP-1, and MIP-1 alpha by spinal perivascular macrophages during experimental allergic . . . BMC Immunol 2002, 3:11.

Christopherson K.W. et al., Endothelial induction of the T-cell chemokine CCL21 in T-cell autoimmune diseases, Blood, Feb. 2003, vol. 101, No. 3, 801-806.

Eugenin E.A. et al., Chemokine-dependent mechanisms of leukocyte trafficking across a model of the blood-brain barrier, Methods 2003, 29:351-361.

Griffith T.S. et al, Monocyte-mediated tumoricidal activity via the tumor necrosis factor-related cytokine, TRAIL, J Exp Med, Apr. 1999, vol. 189, No. 8, 1343-1354.

Wiley S.R. et al., TWEAK, a member of the TNF superfamily, is a multifunctional cytokine that binds the TweakR/Fn14 receptor, Cytokine Growth Factor Rev 2003, 14:241-249.

Zauli G. et al, The role of the TRAIL/TRAIL receptors system in hematopoiesis and endothelial cell biology, Cytokine Growth Factor Rev 2006, 17:245-257.

Kawakita T. et al, Functional expression of TWEAK in human colonic adenocarcinoma cells, Int J Oncol 2005, 26:87-93.

Jin Y.Z. et al., [Adenovirus-mediated CTLA4-FasL gene transfer induces long-term survival of cardiac allograft in rats], Zhonghua Yi Xue Za Zhi 2003, 83:1968-1974, Abstract only.

Schaefer U. et al., TRAIL: a multifunctional cytokine, Front Biosci 2007, 12:3813-3824, Abstract only.

Anel A. et al., Apo2L/TRAIL and immune regulation, Front Biosci 2007, 12:2074-2084 , Abstract only.

Weiss, H.A. et al, CD8+ T cells in inflammatory demyelinating disease, J Neur, 191 (2007), 79-85.

Komiyama, Y. et al., IL-17 plays an important role in the development of experimental autoimmune encephalomyelitis, J Immun, 2006, 177:566-573.

Hofstetter, H.H., et al, Therapeutic efficacy of IL-17 neutralization in murine experimental autoimmune encephalomyelitis, Cellular Immun, 237 (2005) 123-130.

Mahalingam D. et al., TRAIL receptor signalling and modulation: Are we on the right TRAIL?, Cancer Treatment Reviews 35 (2009) 280-288.

Johnstone, R.W. et al., The TRAIL apoptotic pathway in cancer onset, progression and therapy, Nature Reviews Cancer, vol. 8 (2008) 782-798.

Newsom-Davis, T. et al., Is TRAIL the holy grail of cancer therapy?, Cell Death and Disease, Apoptosis (2009) 14:607-623.

Fabregat, I., Dysregulation of apoptosis in hepatocellular carcinoma cells, Word J Gastroenterol, Feb. 7, 2009, 15(5): 513-520.

Kawakita, T., et al., Functional expression of TWEAK in human hepatocellular carcinoma . . . , Biochem and Biophysical Research Comm, 318 (2004) 726-733, Abstract only.

Jakubowski, A, et al., TWEAK induces liver progenitor cell proliferation, J Clinical Investigation, 115:2330-2340 (2005).

* cited by examiner

Figure 2
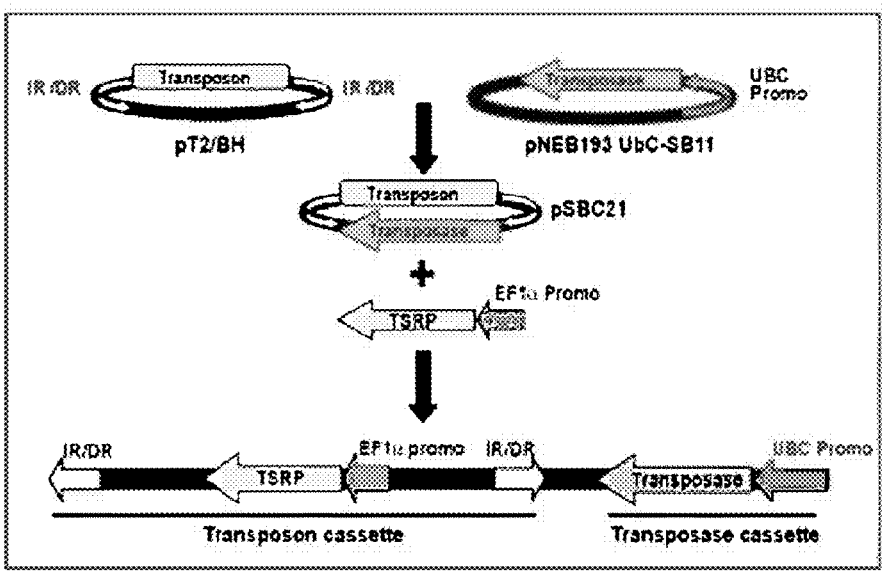
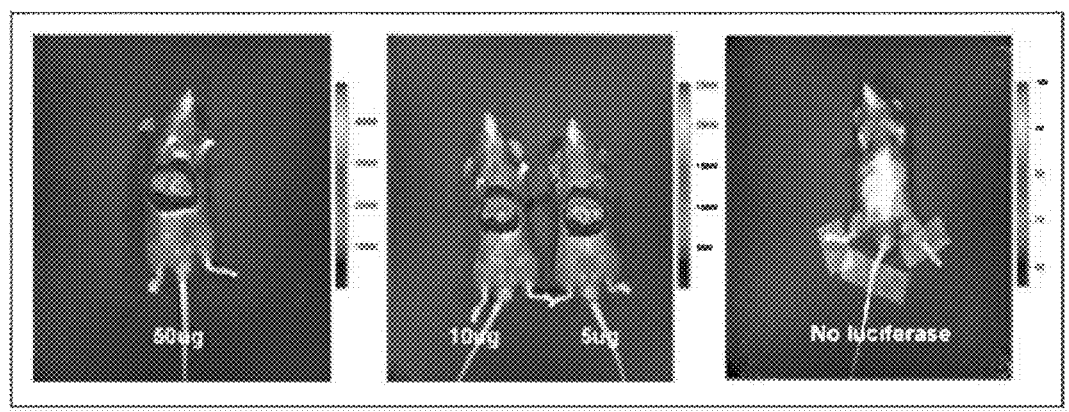
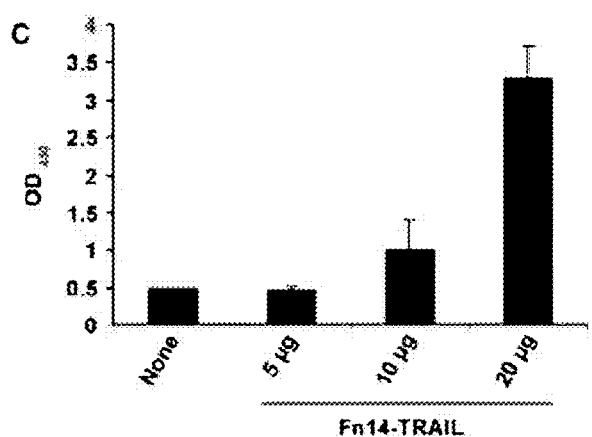

*A.*

*B*

A.

B.

Figure 15
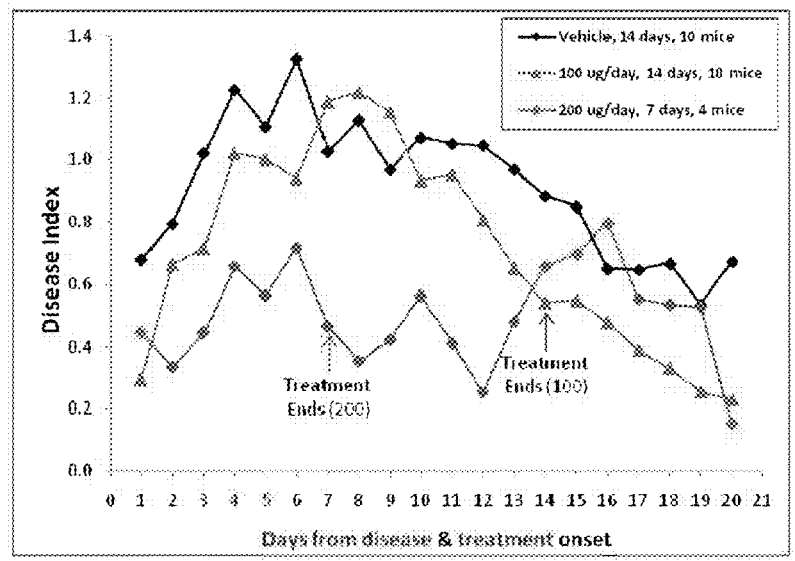
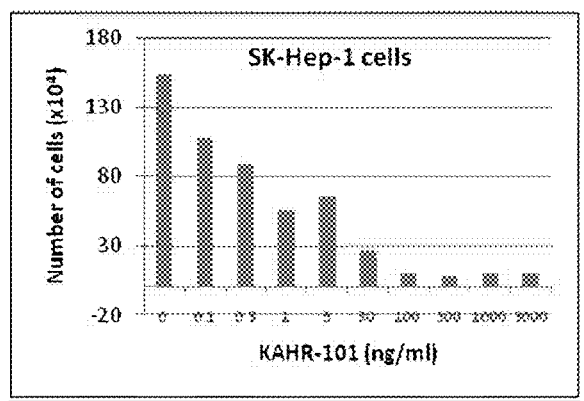
Figure 16A
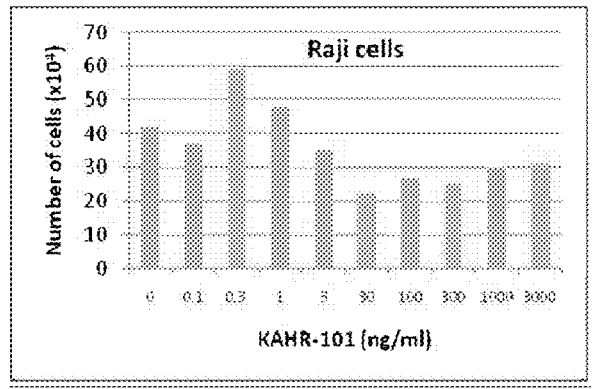
Figure 16B

SEQUENCE LISTING

```
<160> NUMBER OF SEQ ID NOS: 3

<210> SEQ ID NO 1
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Arg
65                  70                  75                  80

Gly Pro Gln Arg Val Ala Ala His Ile Thr Gly Thr Arg Gly Arg Ser
                85                  90                  95

Asn Thr Leu Ser Ser Pro Asn Ser Lys Asn Glu Lys Ala Leu Gly Arg
            100                 105                 110

Lys Ile Asn Ser Trp Glu Ser Ser Arg Ser Gly His Ser Phe Leu Ser
        115                 120                 125

Asn Leu His Leu Arg Asn Gly Glu Leu Val Ile His Glu Lys Gly Phe
    130                 135                 140

Tyr Tyr Ile Tyr Ser Gln Thr Tyr Phe Arg Phe Gln Glu Glu Ile Lys
145                 150                 155                 160

Glu Asn Thr Lys Asn Asp Lys Gln Met Val Gln Tyr Ile Tyr Lys Tyr
                165                 170                 175

Thr Ser Tyr Pro Asp Pro Ile Leu Leu Met Lys Ser Ala Arg Asn Ser
            180                 185                 190

Cys Trp Ser Lys Asp Ala Glu Tyr Gly Leu Tyr Ser Ile Tyr Gln Gly
        195                 200                 205

Gly Ile Phe Glu Leu Lys Glu Asn Asp Arg Ile Phe Val Ser Val Thr
    210                 215                 220

Asn Glu His Leu Ile Asp Met Asp His Glu Ala Ser Phe Phe Gly Ala
225                 230                 235                 240

Phe Leu Val Gly
```

```
<210> SEQ ID NO 2
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Glu
65                  70                  75                  80

Thr Ile Ser Thr Val Gln Glu Lys Gln Gln Asn Ile Ser Pro Leu Val
                85                  90                  95

Arg Glu Arg Gly Pro Gln Arg Val Ala Ala His Ile Thr Gly Thr Arg
            100                 105                 110

Gly Arg Ser Asn Thr Leu Ser Ser Pro Asn Ser Lys Asn Glu Lys Ala
        115                 120                 125

Leu Gly Arg Lys Ile Asn Ser Trp Glu Ser Ser Arg Ser Gly His Ser
    130                 135                 140

Phe Leu Ser Asn Leu His Leu Arg Asn Gly Glu Leu Val Ile His Glu
145                 150                 155                 160

Lys Gly Phe Tyr Tyr Ile Tyr Ser Gln Thr Tyr Phe Arg Phe Gln Glu
                165                 170                 175

Glu Ile Lys Glu Asn Thr Lys Asn Asp Lys Gln Met Val Gln Tyr Ile
            180                 185                 190

Tyr Lys Tyr Thr Ser Tyr Pro Asp Pro Ile Leu Leu Met Lys Ser Ala
        195                 200                 205

Arg Asn Ser Cys Trp Ser Lys Asp Ala Glu Tyr Gly Leu Tyr Ser Ile
    210                 215                 220

Tyr Gln Gly Gly Ile Phe Glu Leu Lys Glu Asn Asp Arg Ile Phe Val
225                 230                 235                 240

Ser Val Thr Asn Glu His Leu Ile Asp Met Asp His Glu Ala Ser Phe
                245                 250                 255

Phe Gly Ala Phe Leu Val Gly
            260

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Trp Tyr Arg Ser Pro Phe Ser Arg Val Val His Leu
1               5                   10
```

FN14/TRAIL FUSION PROTEINS

CROSS-REFERENCE TO RELATED APPLICATION

This application claims priority under 35 U.S.C. §119 (e) to provisional application Ser. No. 61/133,532, filed Jun. 30, 2008, incorporated by reference in its entirety.

GOVERNMENT CONTRACT

This research was supported at least in part by a grant from the National Institutes of Health, grant Nos. RO 1 AI 031044 and RO1 CA 074958. The Government has certain rights in this invention.

FIELD OF THE INVENTION

This invention relates to Fn14/TRAIL and related fusion proteins, and methods of treating certain diseases such as autoimmune diseases and cancer with these proteins.

BACKGROUND INFORMATION

A complex interplay of positive and negative signals regulates T cell activation and maintenance of T cell effector function. Members of the TNF ligand/TNF receptor superfamily figure prominently in this matrix of signals, bridging cells of the immune system, as well as with cells of other organ systems. In so doing, TNF superfamily members contribute to both tissue homeostasis and pathogenesis, via effects on cell survival and death, cellular differentiation, and inflammation. From the standpoint of autoimmune pathogenesis, interesting members of the TNF ligand superfamily are TNF-related apoptosis-inducing ligand (TRAIL), and TWEAK (TNF-related weak inducer of apoptosis).

TRAIL binds to a number of different cognate receptors of the TNF receptor superfamily, some leading to triggering of intracellular signaling pathways and others simply acting as decoy receptors. The triggering receptors in humans are TRAIL-R1, TRAIL-R2, and osteoprotegrin, and in mice the sole triggering receptor is DR5. Virtually all cells of the immune system (T lymphocytes, B lymphocytes, natural killer cells, dendritic cells, monocytes, granulocytes) upregulate surface TRAIL and/or release soluble TRAIL stored in secretory vesicles in response to interferon and other activation signals. TRAIL inhibits autoimmunity in several animal models. Evidence for TRAIL's capacity to inhibit experimental autoimmune encephalitis (EAE), a murine model for MS, has come from experiments invoking TRAIL–/– knockout mice, soluble TRAIL receptor (sDR5) or neutralizing anti-TRAIL mAb capable of blocking TRAIL function, and embryonic stem cell-derived dentritic cells co-expressing TRAIL and pathogenic MOG (myelin oligo-dendrocyte glycoprotein peptide). Interestingly, in MS patients, soluble TRAIL has emerged as a response marker for IFN-β therapy, with those most likely to respond to treatment showing early and sustained soluble TRAIL induction after therapy. Yet, TRAIL's impact on MS/EAE may be more complex, for example, the suggestion that TRAIL may promote brain cell apoptosis. Both TRAIL and FasL have been implicated in negative regulation of T cells.

TWEAK and its counter-receptor Fn14 (fibroblast growth factor-inducible 14 kDa protein) are another TNF family ligand-receptor pair expressed in a range of immune and non-immune cell types, including NK cells, macrophages, dendritic cells, microglial cells, glial cells and endothelial cells. TWEAK promotes the proliferation of some cell types (astrocytes, endothelial cells, and certain human tumor cell lines), and suppresses others (erythroblasts, kidney cells, mesangial cells, neuronal cells, NK cells, monocytes) TWEAK stimulates production of various inflammatory cytokines, chemokines and adhesion molecules. However, the TWEAK.Fn14 signaling axis has effects that go beyond cell proliferation and cytokine production. Interestingly, the richer set of functions linked to TWEAK over the years include ones that tie into autoimmunity. TWEAK increases the permeability of the neurovascular unit, and its endogenous expression is elevated in the CNS during EAE and acute cerebral ischemia. Moreover, TWEAK has pro-angiogenic activity, which is of interest given the association between angiogenesis and autoimmune pathogenesis. TWEAK increases EAE severity and associated neurodegeneration. The induction of inhibitory anti-TWEAK or Fn14 Ab, via vaccination with the extracellular domain of either TWEAK or Fn14, ameliorates EAE manifestations in rat and mouse models.

Multiple sclerosis (MS) is a debilitating neurological disease, and despite an expanding set of treatment options, there remains a pressing need for more effective therapeutic agents. While the precise etiology of MS is unknown, key features of its pathogenesis and clinical evolution are emerging. Pathogenic effector T cells are thought to be pivotal in driving the disease, and thus many therapeutic paths are converging on these cells, with goals such as blocking their activation and re-activation, eliminating them from the larger T cell reservoir, and interfering with their transit to sites of pathogenesis within the CNS.

Both the TWEAK/Fn14 and TRAIL/TRAILR signaling axes have been implicated in cancer. See, e.g., "TRAIL receptor signalling and modulation. Are we on the right TRAIL?", Cancer Treatment Reviews 35 (2009) 280-288; and "The TWEAK-Fn14 cytokine-receptor axis: discovery, biology and therapeutic targeting", Nature 7 (2008) 411-425.

SUMMARY OF THE INVENTION

Accordingly, in one aspect the present invention provides a fusion protein comprising a first domain and a second domain, wherein the first domain is a polypeptide that binds to a TWEAK ligand and the second domain is a polypeptide that binds to a TRAIL receptor.

In an additional aspect, the present invention provides a fusion protein consisting essentially of a first domain and a second domain, wherein the first domain is at least a portion of the extracellular domain of a Fn14 protein and the second domain is at least a portion of the extracellular domain of a TRAIL protein.

In another aspect, the present invention provides a fusion protein comprising a first domain and a second domain, wherein the first domain is a polypeptide that binds to a TWEAK ligand and the second domain is a polypeptide having an inhibitory function.

Pharmaceutical compositions comprising the fusion proteins, as well as methods of treating various illnesses such as autoimmune diseases and cancer, with the fusion proteins of the invention are also provided.

BRIEF DESCRIPTION OF THE DRAWINGS

The invention is further illustrated by the following drawings in which.

A) Western blot analysis was performed on conditioned media from 293 cells transfected with expression constructs for Fn14, Fn14-TRAIL, Fn14-IgG1(mut) and TRAIL. Observed bands were consistent with the expected sizes of 8.7 kD, 27.5 kD, 34.1 kD, and 19.0 kD, respectively.

B) CHO cells were transiently transfected with a murine TWEAK cDNA expression construct, and after 48 h, were incubated at 4° C. with purified Fn14-TRAIL or rTRAIL in sodium azide-containing buffer. The presence of membrane-bound TWEAK on transfectants, and the binding of Fn14-TRAIL to them, was verified by flow cytometry, using anti-mouse TWEAK Ab (B.1) and anti-mouse TRAIL Ab (B.2-5) as detecting Ab, respectively. (B.1) TWEAK is expressed on transfected CHO cells, as detected using anti-TWEAK Ab (solid black line) versus isotype control (filled histogram); (B.2) TRAIL is not detectable on CHO cells, when analyzed using anti-TRAIL Ab (solid black line) versus isotype control (filled histogram). (B.3 and B.4) TRAIL epitopes are enhanced when Fn14-TRAIL is added to TWEAK-expressing, as opposed to TWEAK-negative, CHO cells. Anti-TRAIL Ab and isotype control are represented by solid black line and filled histogram, respectively. (B.5) TWEAK-transfected cells do not bind to anti-TRAIL Ab (solid black line) in the presence of rTRAIL. Isotype control is shown as filled histogram.

C) L929 cells were cultured in flat-bottom 96-well plates at $2 \times 10^4$ cells/well, in 100 µl AIM-V medium. Sixteen hours later, actinomycin D was added to the cultures at 1 mg/well, and cells were cultured for another 2 h. Fn14-TRAIL or rTRAIL, as positive control, was then added, and cultures were maintained for an additional 5 h. The percentage of dead cells was determined by an MTT assay, as described in Materials and Methods.

FIG. 2. Functional validation of the dual cassette pSBC21 vector

A) As schematically depicted, the pSBC21 plasmid incorporates in tandem a transposon cassette (with the EF1α promoter driving the trans signal redirecting protein—TSRP) and a transposase expression cassette (driven by the UBC promoter).

B) Mice were hydrodynamically injected with either pSBC21 vector only (right panel) or the indicated concentrations of pLuciferase•SBC21. Bioluminescent images were acquired after intra-peritoneal administration of D-Luciferin 22 days after plasmid injection. Color bars represent bioluminescent signal in radiance (p/sec/cm²/sr).

C) Serum levels of Fn14-TRAIL were determined by ELISA 20 days after the injection of 5 µg, 10 µg or 20 µg of Fn14-TRAIL•pSBC21 plasmid.

Figure 3:
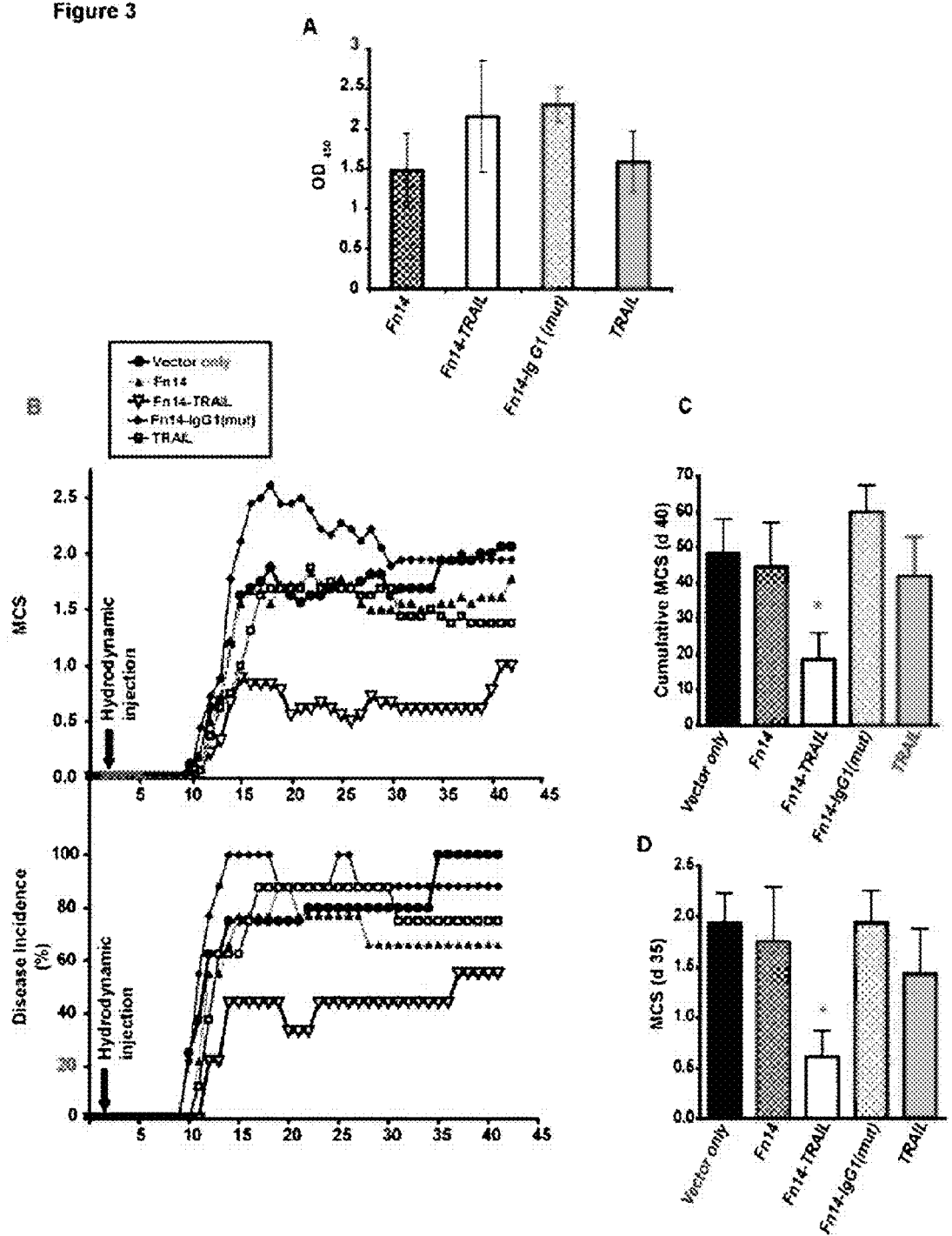

FIG. 3. Fn14-TRAIL suppresses MOG-induced autoimmune encephalomyelitis

A) Serum levels of Fn14, Fn14-TRAIL, Fn14-IgG1 (mut) and TRAIL were measured by ELISA 20 days after hydrodynamically injecting 50 µg of the respective pSBC21-based expression plasmids.

B-D) Mice were challenged with MOG in CFA supplemented with *M. tuberculosis* as described in Material and Methods. 48 h after MOG challenge, mice were hydrodynamically-injected with 50 µg of the indicated pSBC21-based expression constructs. Individual mice were scored according to the clinical scale described in Materials and Methods. Parameters evaluated include mean clinical score (B, upper panel), disease incidence (B, lower panel), cumulative mean clinical score (C) and mean clinical score on day 35 (D). The difference between the Fn14-TRAIL-treated versus vector-only control group is statistically significant according to Mann-Whitney U test ($p<0.05$), where the differences between the other groups shown and the vector-only group are not significant.

Figure 4:
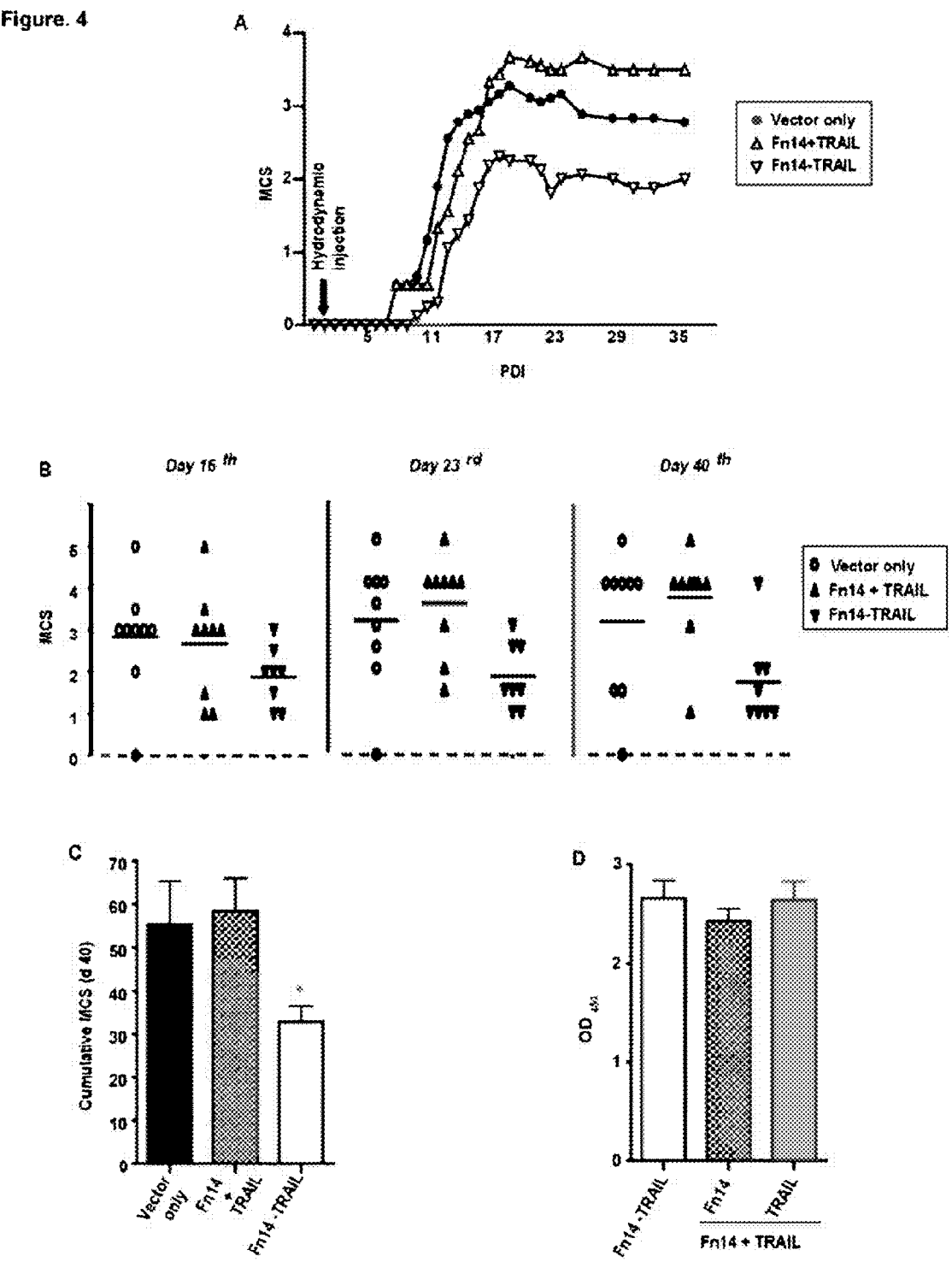

FIG. 4. Fn14 and TRAIL in combination do not achieve Fn14-TRAIL's therapeutic efficacy A-C) 48 h after MOG-challenge, mice were hydrodynamically injected with a single dose of Fn14-TRAIL•pSBC21 plasmid (25 µg/mouse), or a single dose of a mixture of Fn14•pSBC21 and TRAIL•pSBC21 plasmids (25 µg each/mouse). Mean clinical scores for the indicated groups over 40 days (A), and on days 16, 23 and 40(B) are shown. Cumulative MCS of indicated groups at day 40 is also shown (C). The difference between the Fn14-TRAIL-treated versus vector-only control group is statistically significant according to Mann-Whitney U test ($p<0.05$), where the differences between the other groups shown and the vector-only group are not significant.

D) Serum levels of Fn14-TRAIL were determined by ELISA 30 days after the injection of combined Fn14•pSBC21 (25 µg)+TRAIL•pSBC21 (25 µg), or Fn14-TRAIL•pSBC21 (25 µg).

E) MOG-challenged mice that had been hydrodynamically-injected with pSBC21 vector only or Fn14-TRAIL•pSBC21 were sacrificed 43 days after receiving the therapeutic agent. Splenocytes from each mouse were cultured in the presence or absence of different concentrations of $MOG_{38-50}$ peptide, and proliferation was evaluated as described in Materials and Methods. Results are shown as mean±SD from a total of nine mice per group.

Figure 5:
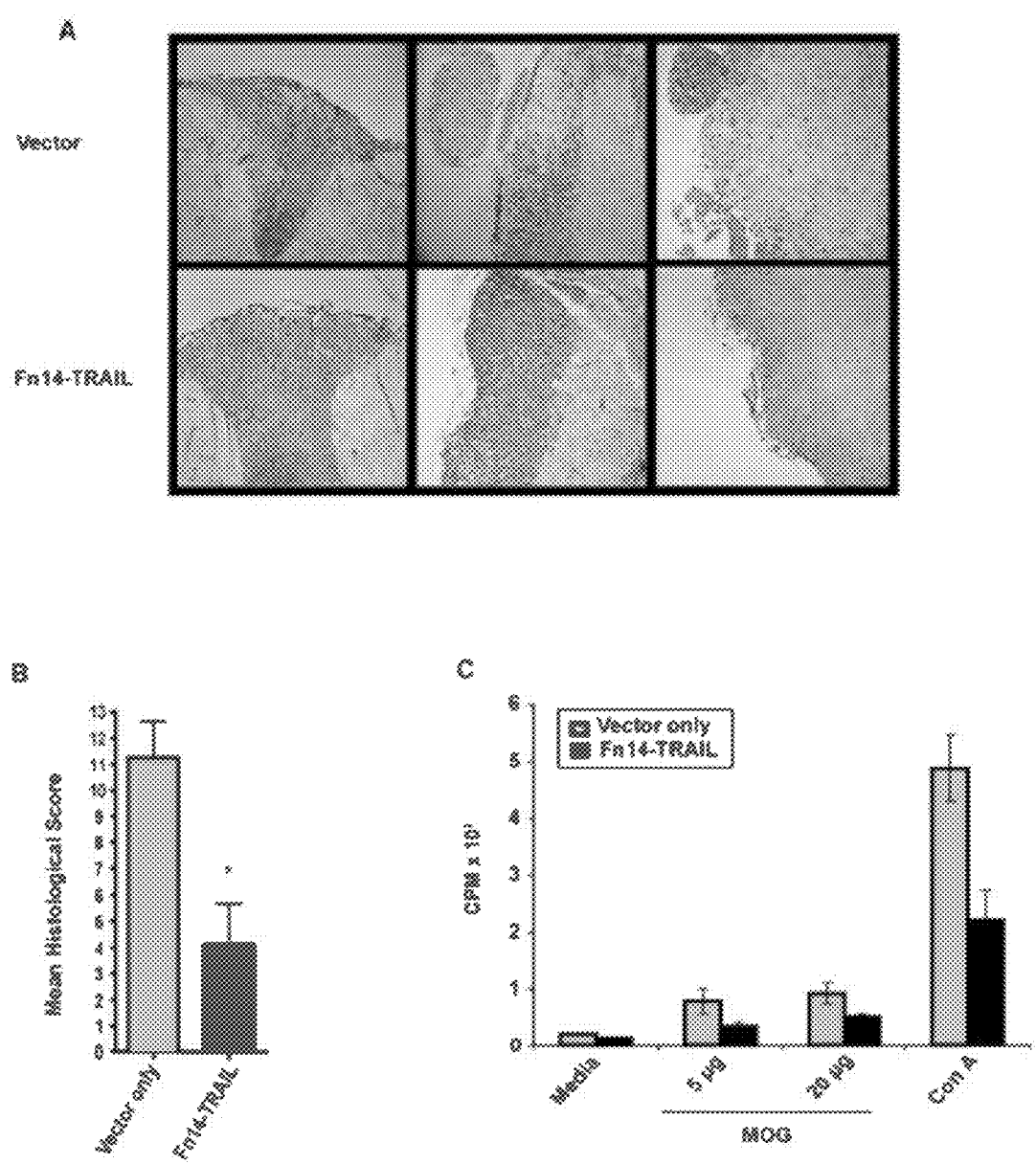

FIG. 5. Fn14-TRAIL•pSBC21 inhibits cytokine production in MOG-challenged mice

Mice were challenged with MOG in CFA supplemented with *M. tuberculosis* and hydrodynamically-injected with pSBC21 vector only or Fn14-TRAIL•pSBC21. Animals were sacrificed 43 days after receiving the therapeutic agent, and splenocytes from each mouse were cultured in the presence or absence of different concentrations of $MOG_{38-50}$ peptide. Cultured media were collected 40 h later, and concentrations of the indicated cytokines were determined by ELISA.

Figure 6:
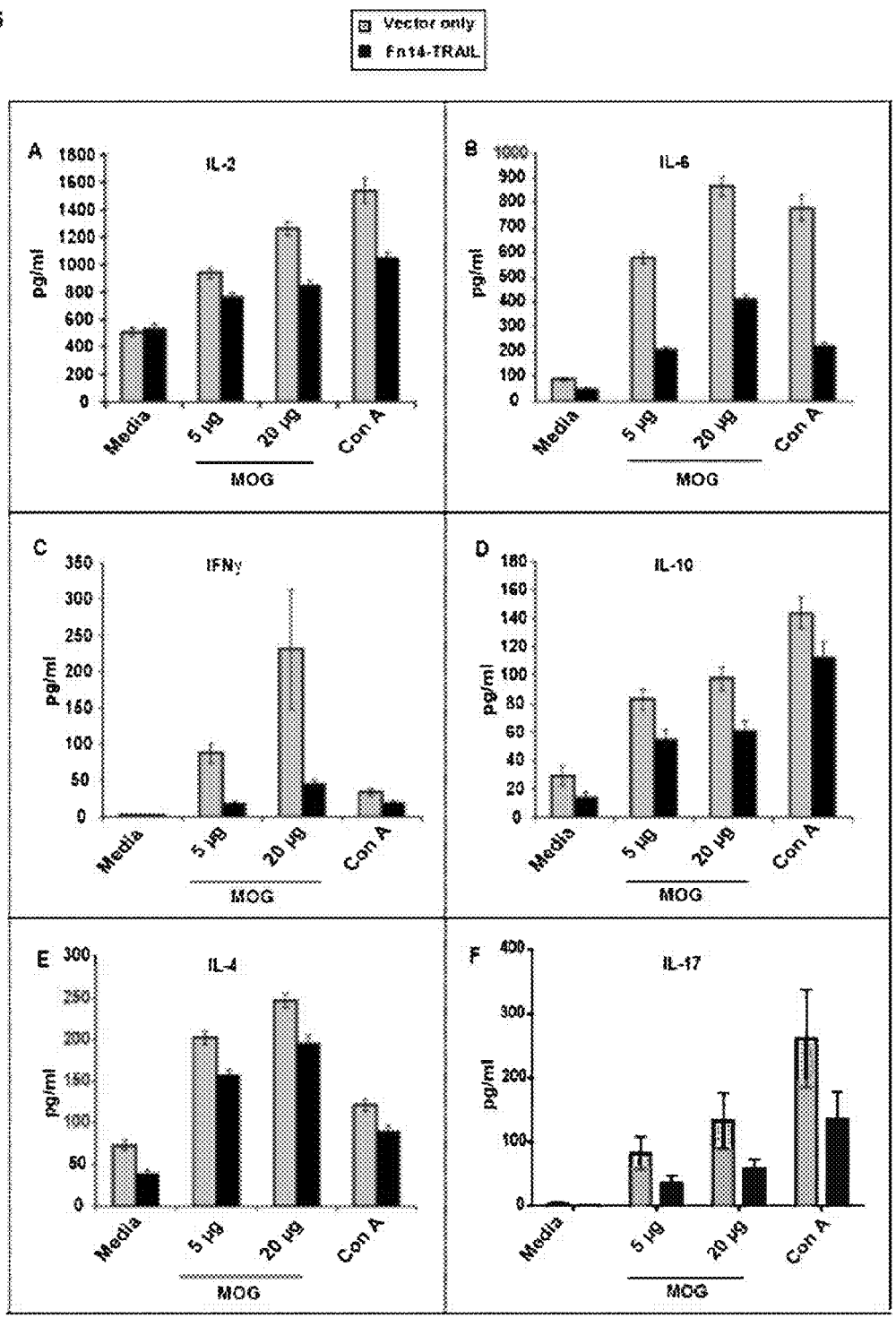

FIG. 6. Fn14-TRAIL•pSBC21 treatment reduces activated and cytokine-producing cells in spinal cords of MOG-challenged mice Infiltrating cells from spinal cords of pSBC21 vector-only and Fn14-TRAIL•pSBC21-treated mice were isolated an analyzed as described in Material and Methods. The number of the cells was calculated by multiplying the total number of live cells by % of each indicated cell type. The percentages and numbers of cells are representative of the percentage and number of the indicated cell types acquired from groups of three mice.

Figure 7:
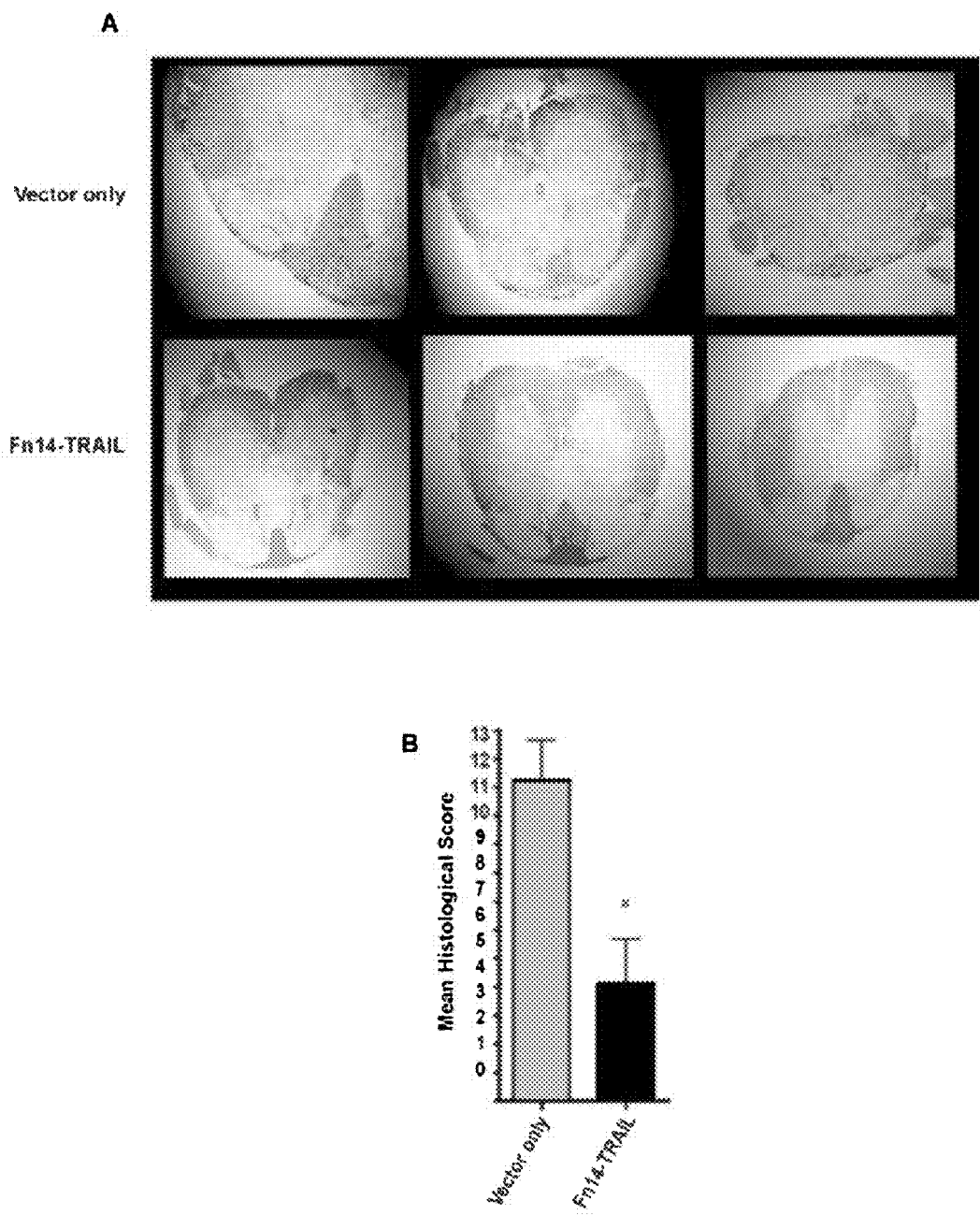

A-B) Percentage and absolute number of activated ($CD69^+$) inflammatory cells on day 7 post-MOG challenge C-D) Percentage and absolute number of $CD4^+$ and $CD8^+$ cells, and of IFNγ, IL-17, and IL-10 expressing cells (amidst activated $CD69^+$, cells or the total cell pool) on day 7 post-MOG challenge D-E) Percentage and absolute number of $CD8^+$ cells and of IFNγ, IL-17 and IL-10 expressing cells on day 14 of post-MOG challenge FIG. 7. Fn14-TRAIL•pSBC21 treatment reduces spinal cord inflammation in MOG-challenged mice MOG-challenged mice, hydrodynamically injected with SBC21 vector only or Fn14-TRAIL•pSBC21, were perfused transcardially with PBS and 10% formalin phosphate. Spinal cords were removed, cut into six pieces, embedded in paraffin, transversely sectioned at 5 μm and stained with luxol fast blue and cresyl violet.

A) Upper panel shows representative spinal cord sections of vector only-treated mice with maximum disease scores of 2, 3.5 and 1 from left to right, respectively. Lower panel shows representative spinal cord sections of Fn14-TRAIL-treated mice with maximum disease scores of 0, 1 and 3 from left to right, respectively.

B) Tissue sections from each of the six spinal cord segments were analyzed for each animal. Scores of inflammation were assigned to individual sections based on the following criteria: 0, no inflammation; 1, <5%; 2, 5-20%; 3, 20-50% and 4, >50% of the white matter is infiltrated by leukocytes. For each mouse, the histological score is the sum of scores from the 6 spinal cord sections. The difference between the Fn14-TRAIL-treated group versus the control group is statistically significant according to Mann-Whitney U test ($p<0.05$).

Figure 8:
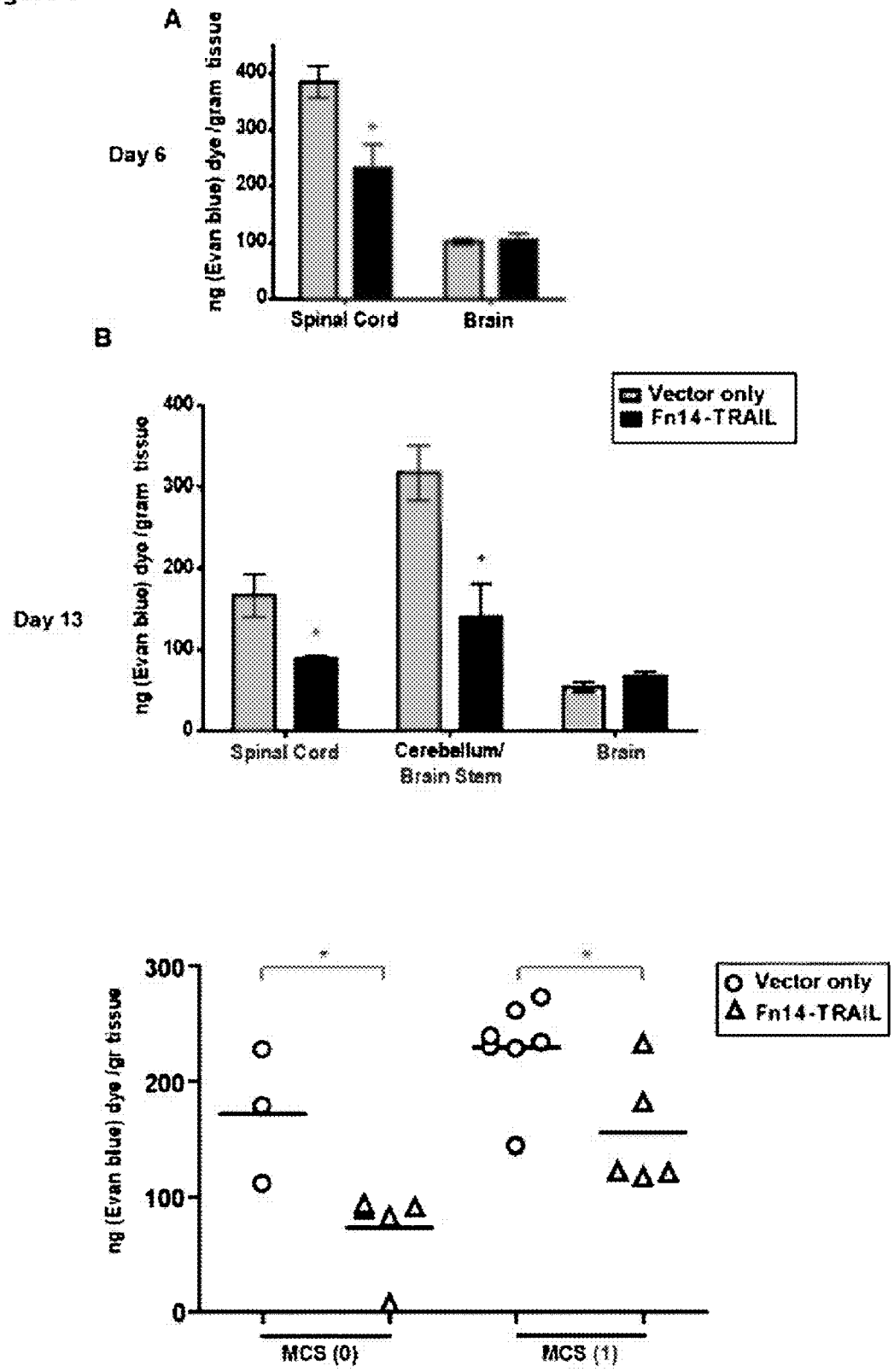

FIG. 8. Fn14-TRAIL treatment reduces blood-brain barrier permeability

MOG-challenged mice, hydrodynamically-injected with SBC21 vector only or Fn14-TRAIL•pSBC21, were injected with Evans blue dye on days 6 (A) or 13 (B) post-MOG challenge. Evans blue was quantitatively analyzed in extracts of the indicated tissues, as described in Materials and Methods. The results represent the specific absorbance of Evans blue at 630 nm calculated as ng/gram tissue. The asterisks indicate that the differences are statistically significant. ($p<0.05$), as determined by Student's t test. In (C), concentrations of absorbed dye in spinal cords of vector only verusus Fn14-TRAIL-treated mice with matched mean clinical scores (0 or 1) on day 13 post-MOG challenge.

Figure 9:
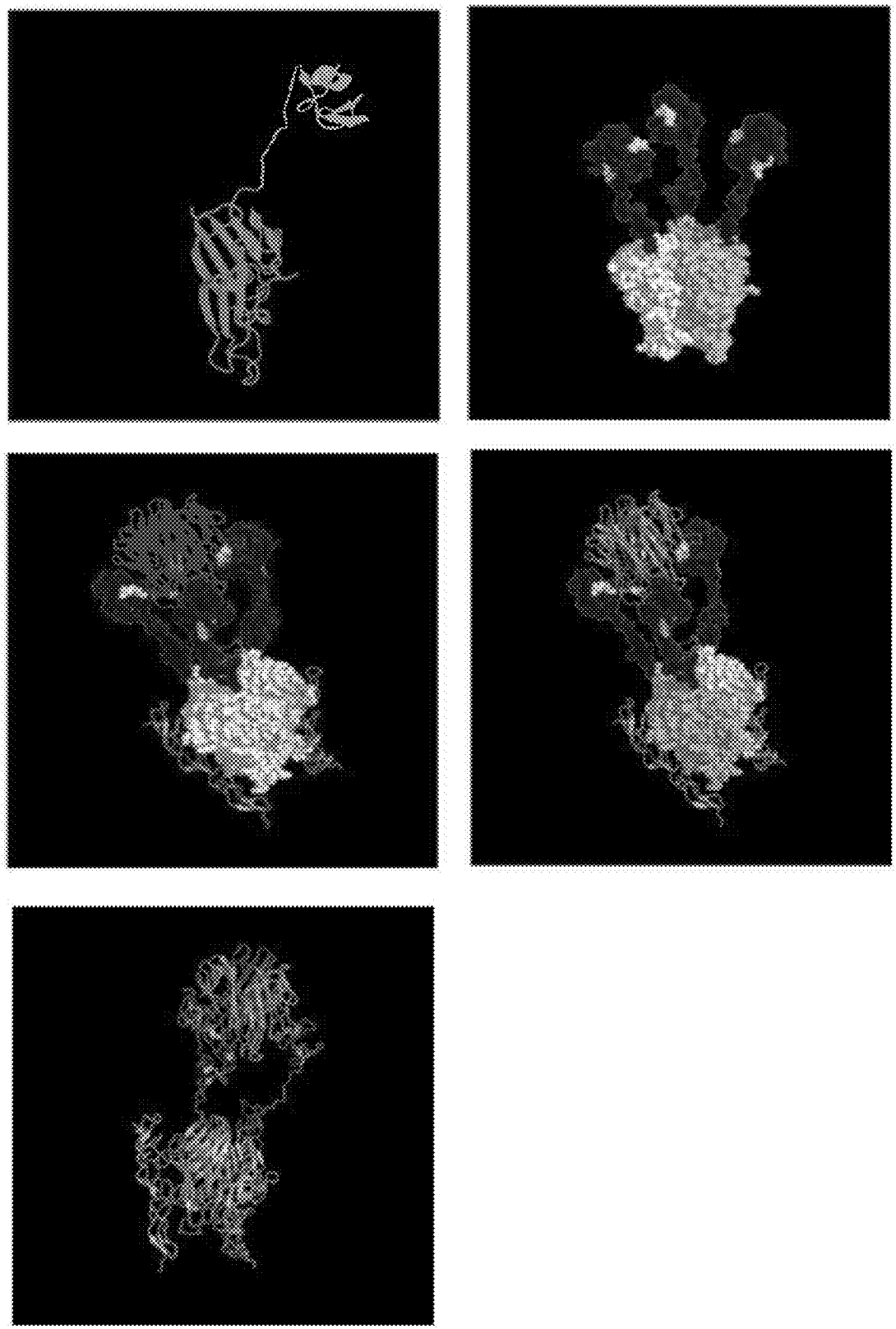

FIG. 9. Structural model of the TWEAK:Fn14-TRAIL; DR5 complex Three-dimensional models, generated as described in Materials and Methods, are shown for Fn14-TRAIL as a monomeric unit (A, Fn14 in blue and TRAIL in white), the Fn14-TRAIL trimer (B, as ribbon model; C, as space-filling model), and the TWEAK:Fn14-TRAIL:DR5 complex (D, with Fn14-TRAIL as space-filling model, TWEAK trimer as ribbon model at top, and DR5 trimer as ribbon model below).

Figure 10:
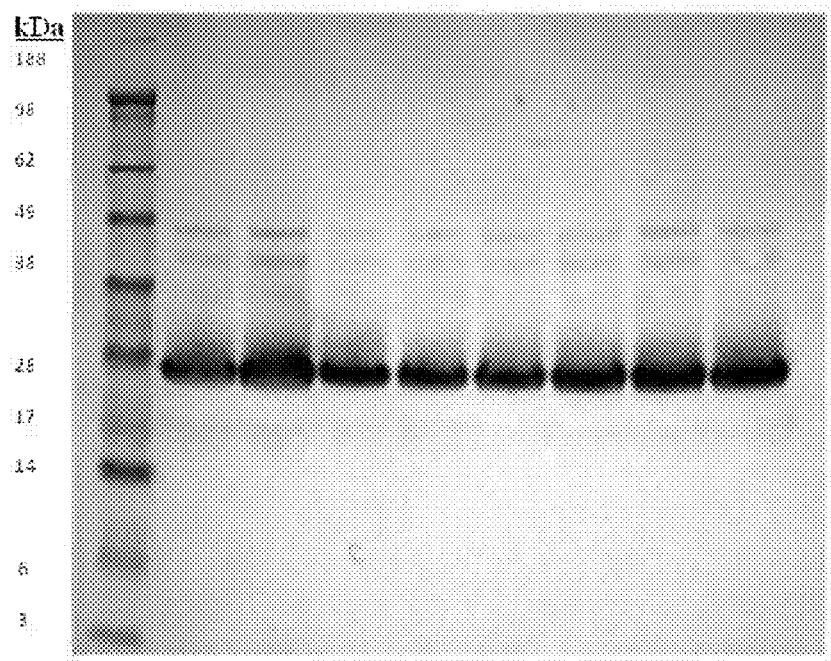

FIG. 10 is a Western blot analysis of human Fn14-TRAIL fusion protein.

Figure 11:
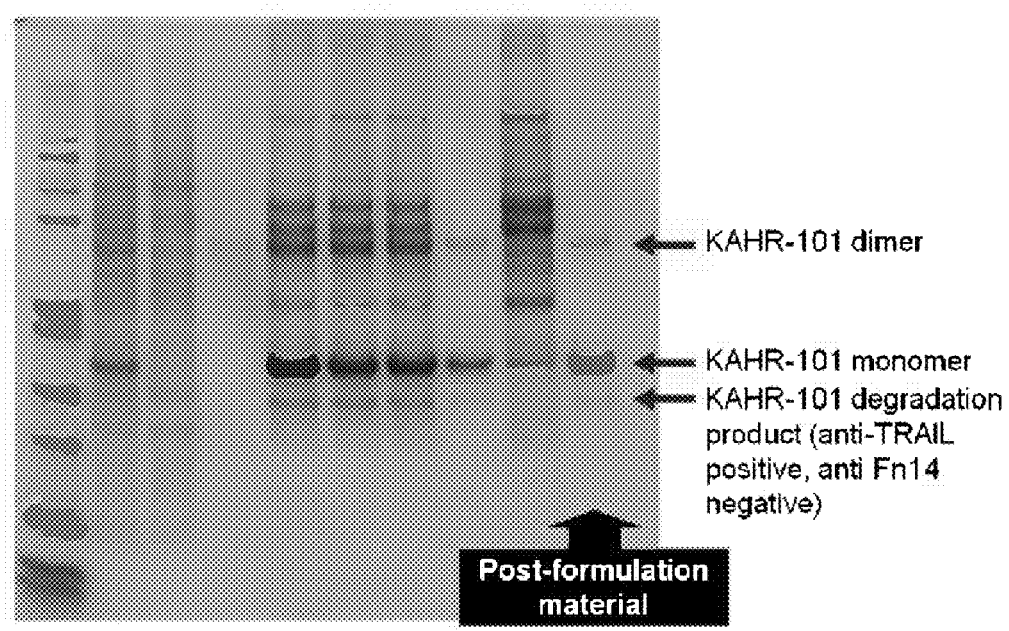

FIG. 11 is an SDS-PAGE analysis showing the products at different sequential steps during the Fn14-TRAIL purification process.

Figure 12A:
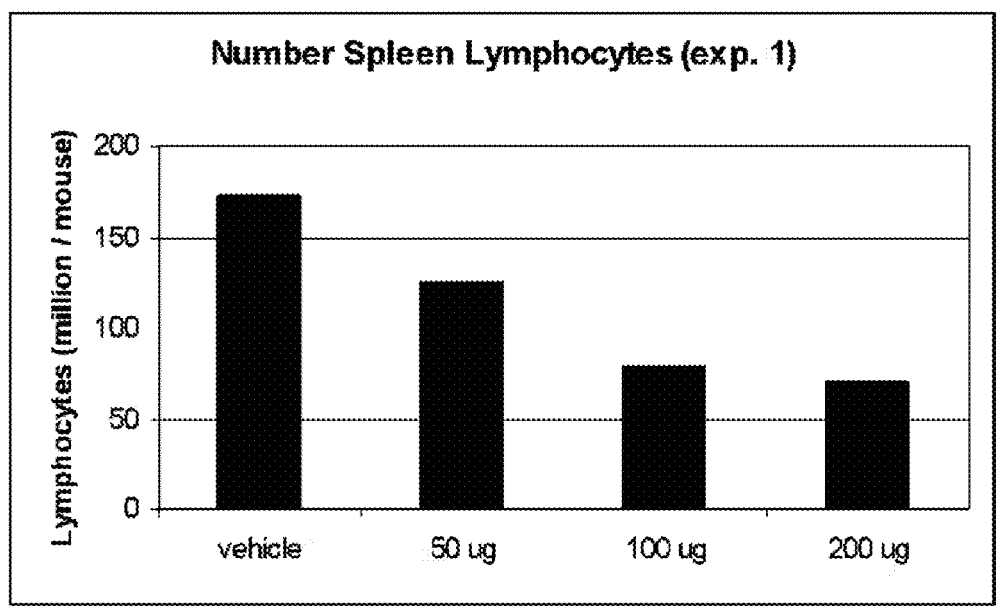
Figure 12B:
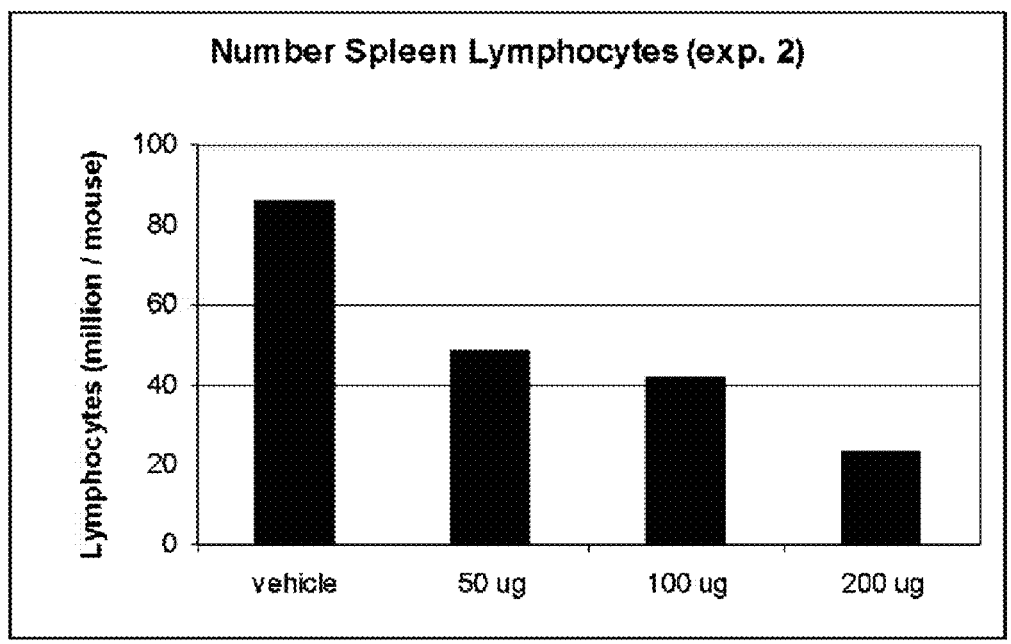

FIG. 12 is a graph of data indicating that Fn14-Trail decreases the total number of splenocytes harvested from MOG-immunized mice.

Figure 13:
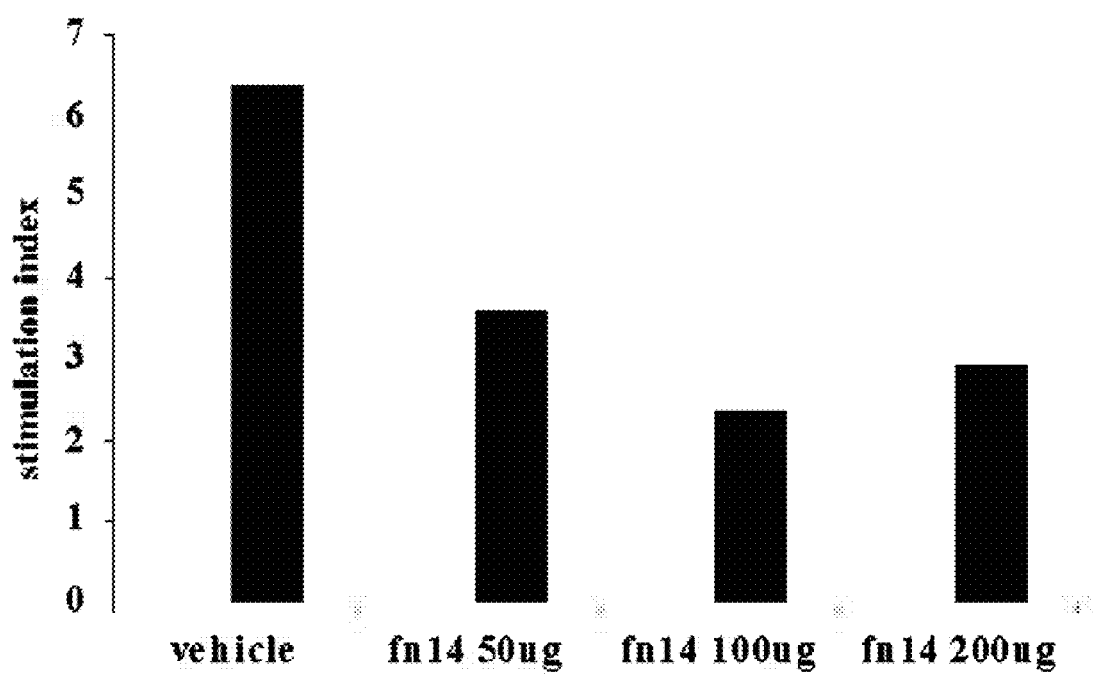

FIG. 13 is a graph of data showing in vivo Fn14-Trail treatment reduces the ex vivo recall response to ex vivo antigenic re-stimulation of lymphocytes recovered from lymph nodes.

Figure 14A:
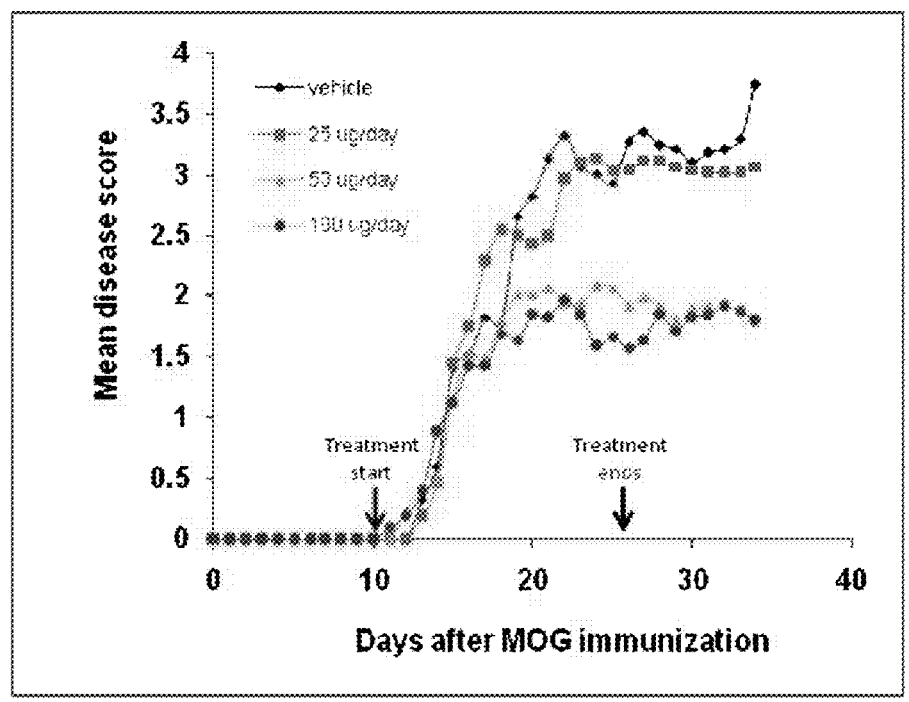
Figure 14B:
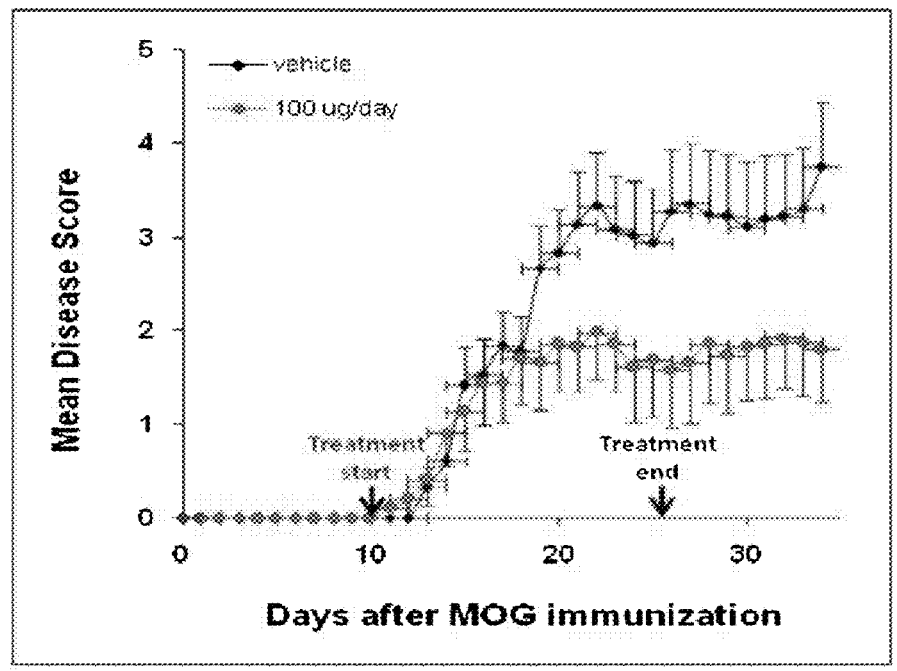

FIGS. 14A-14B are graphs of data showing that Fn14-Trail ameliorates EAE disease progression in MOG-challenged mice.

FIG. 15 is a graph of data indicating that Fn14-Trail inhibits collagen induced arthritis in DBA1 mice.

FIGS. 16A-16D are graphs of data from a SK-HEP1 Hepatoma cell line (A), Raji malignant B cell line (B), and the non-malignant hepatic cell lines NKNT3 (C) and FH-B (D) cultured in the presence of different concentrations of Fn14-TRAIL for 24 hours. Following incubation, cells were collected, stained with trypan blue, and live and dead cells were counted. The data shown is representative of two independent experiments.

Figure 17:
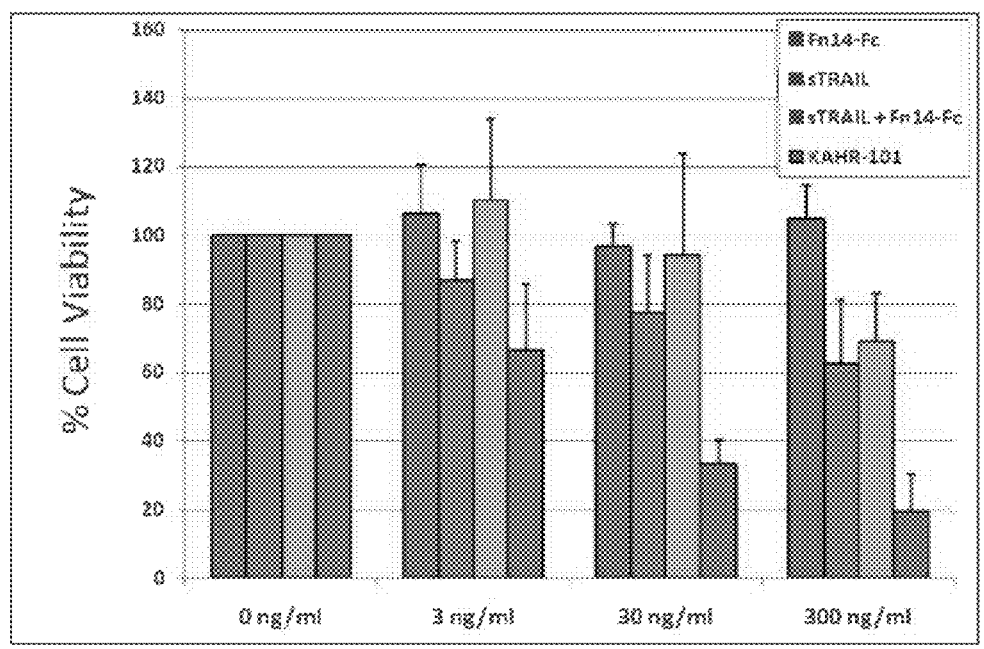

FIG. 17 is a graph of data from a SK-HEP1 Hepatoma cell line cultured in the presence of different concentrations (as shown) of Fn14-TRAIL, sTrail, Fn14-Fc or the combination of the latter two. Following 24 hour incubation, cells were collected, stained with trypan blue, and live and dead cells were counted. The data shown is representative of three independent experiments.

Figure 18:
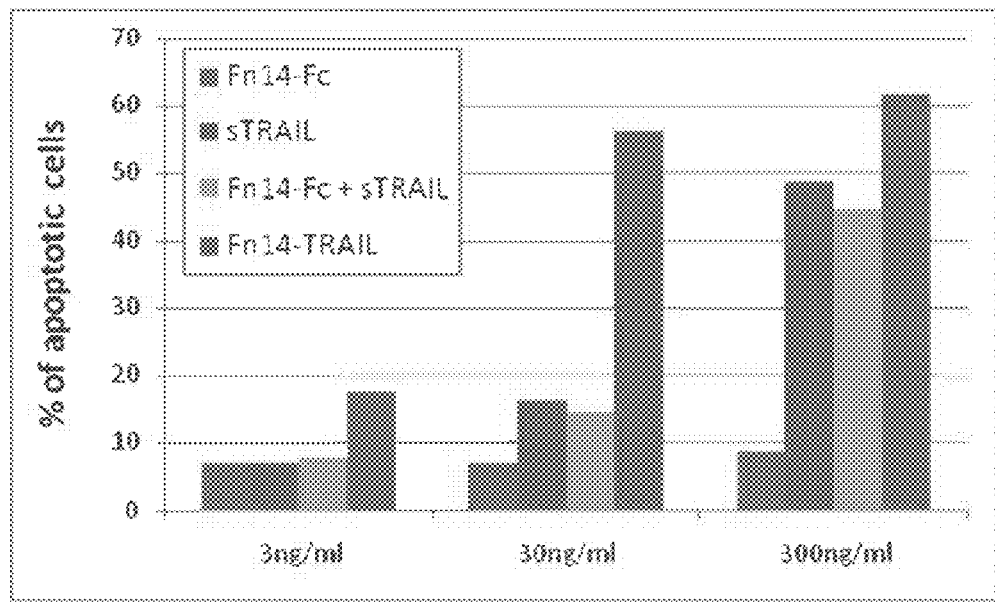

FIG. 18 is a graph of data from a SK-HEP1 Hepatoma cell line cultured in the presence of different concentrations of Fn14-TRAIL, sTRAIL, Fn14-Fc or the combination of the latter two. Following 24 hour incubation, cells were collected and washed, and apoptosis was tested by annexin V/PI staining and flow cytometry. The data shown is representative of two independent experiments.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein. Where any amino acid sequence is specifically referred to by a Swiss Prot. or NCBI Accession number, the sequence is incorporated herein by reference.

The present invention provides, in one aspect, a fusion protein which acts on the TWEAK and TRAIL signaling axes, for example a fusion protein having a first domain that comprises a polypeptide that binds to a TWEAK ligand; and a second domain that comprises a polypeptide that binds to the TRAIL receptor.

In particular, the first domain is a polypeptide that has the capacity to interfere with TWEAK's ability to trigger through its Fn14 receptor, and the second domain is a polypeptide that can direct inhibitory signals through cognate receptors on T cells or other cells bearing the TRAIL receptor.

Suitable first domains in the context of the TWEAK and TRAIL signaling axes include, for example, the Fn14 protein, variants or derivatives of the wild-type Fn14 protein, or other polypeptides or proteins specifically tailored to bind TWEAK and prevent this ligand from signaling through its Fn14 receptor, such as antibodies that bind to TWEAK, parts of antibodies that bind to TWEAK, and lipocalin derivatives engineered to bind to TWEAK. Preferably, the first domain of the fusion protein of this embodiment is at least a portion of the extracellular domain of the Fn14 protein, specifically that portion of the extracellular domain which is necessary for binding to the TWEAK ligand and interfering with its ability to bind and trigger a membrane-bound Fn14 receptor. Variants of the wild-type form of the extracellular domain, or the portion of the extracellular domain responsible for TWEAK binding, are also included in the present invention, so long as the variant provides a similar level of biological activity as the wild-type protein.

Accordingly, the term "polypeptide that binds to a TWEAK ligand" as used herein includes the Fn14 protein; the extracellular domain of the Fn14 protein; a polypeptide which is at least a portion of the extracellular domain of the Fn14 protein, the portion responsible for binding to a TWEAK ligand; antibodies or parts of antibodies to TWEAK; lipocalin derivatives; and variants and/or derivatives of any of these. The term "Fn14" is understood to embrace polypeptides corresponding to the complete amino acid sequence of the Fn14 protein, including the cytoplasmic, transmembrane and extracellular domains, as well as polypeptides corresponding to smaller portions of the protein, such as the extracellular domain, or a portion of the extracellular domain. In one embodiment the first domain of the Fn14/TRAIL fusion protein is at least a portion of the extracellular domain of the human Fn14 protein.

Suitable second domains in the context of the TWEAK and TRAIL signaling axes include, for example, the TRAIL protein itself, variants or derivatives of the TRAIL protein, or other polypeptides or proteins that are specifically designed to inhibit activation of T cells or other cells and/or induce apoptosis through the TRAIL receptor, such as agonistic anti-TRAIL Ab, and variants and/or derivatives of any of these.

Preferably, the second domain of the fusion protein in this embodiment is at least a portion of the extracellular domain of the TRAIL protein, specifically that portion which is necessary for binding to a TRAIL receptor. Variants of the wild-type form of the extracellular domain of the TRAIL protein, or the portion of the extracellular domain responsible for TRAIL receptor binding, are also included in the present invention, so long as the variant provides a similar level of biological activity as the wild-type protein.

Accordingly, the term "polypeptide that binds to a TRAIL receptor" as used herein includes the TRAIL protein; the extracellular domain of the TRAIL protein; a polypeptide which is at least a portion of the extracellular domain of the TRAIL protein, the portion responsible for binding to a TRAIL receptor; antibodies (and parts of antibodies) to a TRAIL receptor; and variants and/or derivatives of any of these. The term "TRAIL" is understood to embrace polypeptides corresponding to the complete amino acid sequence of the TRAIL protein, including the cytoplasmic, transmembrane and extracellular domains, as well as polypeptides corresponding to smaller portions of the protein, such as the extracellular domain, or a portion of the extracellular domain. In one embodiment the second domain of Fn14-TRAIL fusion protein is at least a portion of the extracellular domain of the human TRAIL protein.

In one embodiment, the present invention comprises a Fn14/TRAIL fusion protein. In another embodiment, the term "Fn14/TRAIL fusion protein" refers to the specific fusion protein identified by SEQ. ID. NO.1:

HUMAN Fn14-TRAIL
SEQ. ID. NO. 1
MARGSLRRLLRLLVLGLWLALLRSVAGEQAPGTAPCSRGSSWSADLDKCM

DCASCRARPHSDFCLGCAAAPPAPFRLLWRGPQRVAAHITGTRGRSNTLS

SPNSKNEKALGRKINSWESSRSGHSFLSNLHLRNGELVIHEKGFYYIYSQ

TYFRFQEEIKENTKNDKQMVQYIYKYTSYPDPILLMKSARNSCWSKDAEY

GLYSIYQGGIFELKENDRIFVSVTNEHLIDMDHEASFFGAFLVG

In another embodiment, the term "Fn14/TRAIL fusion protein" refers to the specific fusion protein identified by SEQ. ID. NO.2.

HUMAN Fn14-TRAIL
SEQ. ID. NO. 2
MARGSLRR LLRLLVLGLWLALLRSVAGEQAPGTAPCSRGSSWSADLDKC

MDCASCRARPHSDFCLGCAAAPPAPFRLLWETISTVQEKQQNISPLVRER

GPQRVAAHITGTRGRSNTLSSPNSKNEKALGRKINSWESSRSGHSFLSNL

HLRNGELVIHEKGFYYIYSQTYFRFQEEIKENTKNDKQMVQYIYKYTSYP

DPILLMKSARNSCWSKDAEYGLYSIYQGGIFELKENDRIFVSVTNEHLID

MDHEASFFGAFLVG

Both SEQ. ID NO. 1 and SEQ. ID. NO. 2 include original signal peptides, these signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

In additional embodiments, the Fn14/TRAIL fusion protein is a variant and/or derivative of the amino acid sequence shown in SEQ.ID.NO. 1 or SEQ. ID. NO.2.

In yet an additional aspect of the present invention, the TRAIL component of any of the fusion proteins described herein can be substituted with another inhibitory protein, i.e. a protein which prevents activation of an immune response and/or induces apoptosis in T cells or other cell types, such as B cells, natural killer (NK) cells, NKT cells, lymphoid progenitor cells, dendritic cells, monocytes/macrophages, tissue-based macrophage lineage cells with antigen-presenting capacity, and any one of a number of non-professional antigen-presenting cells, for example, endothelial cells. Examples of inhibitory proteins include, but are not limited to, FasL, TNF, PDL-1, PDL-2, B7x, B7-H3 and CD31.

For example, BTLA is an important inhibitory receptor, and B7x may be the ligand, in addition to other ligands as yet to be discovered. Similarly, CTLA-4 is another important inhibitory receptor, and ligands that drive this inhibitory CTLA-4 receptor include some of the B7 molecules, as well as agonist Ab. In this case the fusion proteins would be Fn14/B7x and Fn14/B7 agonist fusion proteins, respectively.

There is growing appreciation that B cells may also be key for driving autoimmunity. Additional inhibitory ligands (fused to Fn14) that drive B cell inhibitory receptors, such as CD100 (binds to CD72), CD5 (also binds to CD72), CD72 (binds to CD5), Ep-CAM (binds to LAIR-1), agonists for FcgammaRII, CD22, PDL-1, PDL-2, CD66a, and PIR-B are also included within the scope of the present invention.

The literature is replete with additional examples, such as those listed in Sinclair, N. "*Why so Many Coinhibitory Receptors?*, Scand. J. Immunol. 50, 10-13 (1999), Melero, I. et al. "*Immunostimulatory monoclonal antibodies for cancer therapy*", Nature Rev. Cancer 7:95-106 (2007), and Zang, X. et al., "*The B7 Family and Cancer Therapy: Costimulation and Coinhibition*", Clin. Cancer Res. 13: 5271-5279 (2007), all incorporated herein by reference. Any of the above mentioned inhibitory proteins are embraced by the fusion proteins and methods of the present invention, and are referred to herein collectively as "polypeptides having an inhibitory function".

Accordingly, in additional embodiments the present invention provides Fn14/inhibitory protein fusion pairs, such as Fn14/FasL, Fn14/PDL-1, Fn14/PDL-2, Fn14/TNF, Fn14/CD100, Fn14/CD5, Fn14/CD72, Fn14/Ep-CAM, Fn14/Fc-gamma-RII, Fn14/CD22, Fn14/CD66a, Fn14/PIR-B, Fn14/B7x, Fn14/B7-H3 and Fn14/CD31. Any of the first domains described above in the context of the TWEAK/TRAIL signaling axes, e.g. polypeptides that bind to a TWEAK ligand, would be suitable first domains in these embodiments.

In one embodiment, the fusion proteins of the present invention inhibit activation of the immune system by preventing or reducing proliferation and differentiation of myelin-specific T cells. In some embodiments the fusion proteins of the present invention inhibit production of pro-inflammatory cytokines and chemokines, such as IL-6, IL-8, RANTES, IP-10, and MCP-1, or inhibit potentiation of other cytokines/chemokines, such as TNF-α and IL-1β; or inhibit induction of matrix metalloproteinases such as MMP-1 and MMP-9; or inhibit prostaglandin E2 secretion from fibroblasts and synoviocytes. The present invention embraces inhibition/downregulation of any and all cytokines that are either promoted by TWEAK ligand or down-modulated by the TRAIL ligand.

In other embodiments the fusion proteins of the present invention inhibit autoreactive T cell proliferation, autoreactive antibody production, and inflammatory reactions.

In additional embodiments, the fusion proteins of the present invention reduce inflammation as determined in in vitro and in vivo assays that measure inhibition of pro-inflammatory cytokine and chemokine production and/or elevation of anti-inflammatory cytokine production, in in vivo model systems of inflammation, such as autoimmune disease models, for example, EAE and collagen-induced arthritis, and delayed-type hypersensitivity and other models in which pro-inflammatory agents are introduced locally or systemically into animals. In these in vivo models, inflammation is assessed by histological examination of inflamed tissues, isolation of inflammatory cells from diseased tissues, and measurement of disease manifestations in affected animals. The fusion proteins of the present invention, in other embodiments, inhibit the proliferation, differentiation and/or effector function of pathogenic T cells such as autoreactive $CD4^+$ T cells and $CD8^+$ T cells and other pathogenic immune cells such as B cells, natural killer (NK) cells, NKT cells, lymphoid progenitor cells, dendritic cells, monocytes/macrophages; induce apoptosis in pathogenic immune cells; promote generation of immune cells with regulatory properties (such as $CD4^+$ $CD25^+$ regulatory T cells, Tr1 cells, $CD8^+$, NK NKT, and dendritic cells with immuno-inhibitory activities); decrease permeability of the blood-brain barrier, and thereby restrict access of inflammatory cells to the CNS; decrease access of inflammatory cells to other disease sites, and decrease angiogenesis associated with inflammation.

As described above, TWEAK ligand is expressed on a range of immune and non-immune cell types, including NK cells, macrophages, dendritic cells, microglial cells, glial cells and endothelial cells. Hence, by interfering with TWEAK signals from these cells, Fn14-bearing fusion proteins block TWEAK-mediated signals directed by each of these cell types to the various Fn14-bearing cells they interact with. As also mentioned above, TWEAK promotes the proliferation of some Fn14-bearing cell types, such as astrocytes, endothelial cells, and certain human tumor cell lines, and suppresses others, such as erythroblasts, kidney cells, mesangial cells, neuronal cells, NK cells, monocytes, and hence, Fn14-containing fusion proteins can reverse these TWEAK-driven biological effects. Furthermore, since Fn14/TRAIL fusion proteins are functioning to exchange and re-direct intercellular signals, other cell targets are TRAIL-receptor bearing cells that are being actively inhibited such as T cells and other TRAIL-R bearing cells including variety of tumor cell types, such as breast, ovarian, prostate, colon, myeloma, glioblastoma and leukemia cancers.

Fn14

Fn14 is a plasma membrane-anchored protein and a TNFR (TNF receptor) superfamily member of 129 amino acids in length (Swiss Prot Accession number Q9CR75 (mouse) and Q9NP84 (human). Two variants of Fn14 are known, identified by Swiss Prot. Isoform ID Nos. Q9NP84.1 and Q9NP84.2 (NCBI accession numbers are NP_057723 and BAB17850, respectively). The Fn14 sequence has also been determined in many other species, including *Xenopus laevis* (NCBI Accession No. AAR21225) and rat (NCBI Accession No. NP_851600].

Most TNFR superfamily members contain an extracellular domain that is structurally characterized by the presence of one to six cysteine-rich domains (CRDs). The typical CRD is approximately 40 amino acids in length and contains six conserved cysteine residues that form three intrachain disulphide bridges. The CRD itself is typically composed of two distinct structural modules.

Fn14 is a Type I transmembrane proteins that contains a 53-amino-acid extracellular domain, amino acids 28-80, with one CRD. Certain charged amino acid residues within this CRD have been shown to be particularly critical for an effective TWEAK-Fn14 interaction. Brown, S. A. et al., *Tweak binding the Fn14 cysteine-rich domain depends on charded residues located in both the A1 and D2 modules*, J. Biochem. 397: 297-304 (2006), incorporated herein by reference.

Based on the information provided in the Brown et al. article, for example, one skilled in the art can determine which variants of the Fn14 protein will retain TWEAK binding activity and which ones will not. For example, several specific variants prepared by site-specific mutations at positions that were not evolutionarily conserved were found to have TWEAK binding activity. In contrast, at least three amino acids in the CRD region were critical for TWEAK binding. By comparing the amino acid sequences of the Fn14 protein in a variety of species one can determine which amino acid positions are not highly conserved, and would be good candidates for substitution/addition/deletion. Substitutions/deletions/additions in highly conserved regions, particularly in the TNFR homology region, would not be considered likely candidates for preparation of variants according to the present invention.

TRAIL

TRAIL is a Type II membrane protein having 291 amino acids and has been sequenced in a number of species, including, but not limited to, mouse: Swiss Prot. Accession No. P50592: human: Swiss Prot. Accession No. P50591, *Rattus norvegicus*: NCBI Accession NP_663714; *Siniperca Chuatsi* (Chinese Perch): NCBI Accession AAX77404; *Gallus Gallus* (Chicken): NCBI Accession BAC79267; *Sus Scrofa* (Pig): NCBI Accession NP_001019867; *Ctenopharyngodon Idella* (Grass Carp): NCBI Accession AAW22593; and *Bos Taurus* (Cattle): NCBI Accession XP_001250249.

The extracellular domain of TRAIL comprises amino acids 39-281, and the TNF domain responsible for receptor binding is amino acid 121-280, based on TNF homology models. The portion of the protein that is particularly important for conferring activity has been identified. See, e.g., "*Triggering cell death: The crystal structure of Apo2L/TRAIL in a complex with death receptor*", Hymowitz S G, et al., Am. Mol. Cell. 1999 October; 4(4):563-71), incorporated herein by reference, which reports the most important amino acids for TRAIL binding to its receptor and activity are amino acids around the zinc area such as amino acids (191-201-205-207-236-237) and amino acids (150-216), incorporated herein by reference. See also 1) Krieg A et al 2003 Br. J of Cancer 88: 918-927, which describes two human TRAIL variants without apoptotic activity, TRAIL-γ and TRAIL β; 2) "*Enforced covalent trimerization increases the activity of the TNF ligand family members TRAIL and CD95L*", D Berg et al., Cell death and differentiation (2007) 14, 2021-2034; and 3) "Crystal Structure of TRAIL-DR5 *complex identifies a critical role of the unique frame insertion in conferring recognition specificity*", S. Cha et al., J. Biol. Chem. 275: 31171-31177 (2000), all incorporated herein by reference.

TRAIL is known to ligate two types of receptors: death receptors triggering TRAIL-induced apoptosis and decoy receptors that possibly inhibit this pathway. Four human receptors for TRAIL have been identified, including TRAILR1, TRAILR2, TRAILR3 and TRAILR4. TRAIL can also bind to osteoprotegerin (OPG). Binding to each of these receptors has been well-characterized. See, e.g., "*The TRAIL apoptotic pathway in cancer onset, progression and therapy*", Nature Reviews Cancer Volume 8 (2008) 782-798.

ADDITIONAL DEFINITIONS

As used herein, the term "fusion proteins" refers to chimeric proteins comprising amino acid sequences of two or more different proteins. Typically, fusion proteins result from in vitro recombinatory techniques well known in the art.

As used herein, "biologically active or immunologically active" refers to fusion proteins according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type proteins which are the building blocks of the fusion proteins of the present invention.

As used herein, a "deletion" is defined as a change in amino acid sequence in which one or more amino acid residues are absent as compared to the wild-type protein.

As used herein an "insertion" or "addition" is a change in an amino acid sequence that has resulted in the addition of one or more amino acid residues as compared to the wild-type protein.

As used herein "substitution" results from the replacement of one or more amino acids by different amino acids, respectively, as compared to the wild-type protein.

As used herein, the term "variant" means any polypeptide having a substitution of, deletion of or addition of one (or more) amino acid from or to the sequence (or any combination of these), including allelic variations, as compared with the wild-type protein, so long as the resultant variant fusion protein retains at least 75%, 80%, 85%, 90%, 95%, 99% or more of the biological or immunologic activity as compared to the wild-type proteins as used in the present invention. Typically, variants of the FN14/TRAIL fusion protein embraced by the present invention will have at least 80% or greater sequence identity or homology, as those terms are understood in the art, to SEQ. ID. NO. 1 or SEQ. ID. NO. 2, more preferably at least 85%, 86%, 87%, 88%, 89%, 90%, 91%, 92%, 93%, 94%, 95%, 96%, 97%, 98%, or even 99% sequence identity to SEQ. ID. NO. 1 or SEQ. ID. NO. 2.

Sequence identity or homology can be determined using standard techniques known in the art, such as the Best Fit sequence program described by Devereux et al., Nucl. Acid Res. 12:387-395 (1984) or the BLASTX program (Altschul et al., J. Mol. Biol. 215, 403-410). The alignment may include the introduction of gaps in the sequences to be aligned. In addition, for sequences which contain either more or fewer amino acids than the proteins disclosed herein, it is understood that the percentage of homology will be determined based on the number of homologous amino acids in relation to the total number of amino acids.

Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity, for example, to diminish neurotoxicity. Moreover, variants or derivatives can be generated that would bind more selectively to one of the TRAIL receptor variants (there are three TRAIL receptors in humans). Furthermore, variants or derivatives can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence. Conservative amino acid substitutions may be made, for example from 1, 2 or 3 to 10, 20 or 30 substitutions provided that the modified sequence retains the ability to act as a fusion protein in accordance with present invention. Amino acid substitutions may include the use of non-naturally occurring analogues, for example to increase blood plasma half-life.

Conservative substitutions are known in the art, for example according to the table below. Amino acids in the same block in the second column and preferably in the same line in the third column may be substituted for each other:

| ALIPHATIC | Non-polar | GAPILV |
|-----------|-----------|--------|
|           | Polar - uncharged | CSTM |
|           |           | NQ |
|           | Polar - charged | DE |
|           |           | KR |
| AROMATIC  |           | HFWY |

The term "derivative" as used herein in relation to the amino acid sequence means chemical modification of a fusion protein of the invention.

Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Additional modifications can include, for example, production of a fusion protein conjugated with polyethylene glycol (PEG), or addition of PEG during chemical synthesis of a polypeptide of the invention.

Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylations site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis [Gillman et al., Gene 8:81 (1979); Roberts et al., Nature 328:731 (1987) or Innis (Ed.), 1990, PCR Protocols: A Guide to Methods and Applications, Academic Press, New York, N.Y.] or the polymerase chain reaction method [PCR; Saiki et al., Science 239:487 (1988)], as exemplified by Daugherty et al. [Nucleic Acids Res. 19:2471 (1991)] to modify nucleic acids encoding the complete receptors.

Additional modifications can be introduced such as those that further stabilize the TRAIL trimer and/or increase affinity of binding to the TRAIL receptor; and spacers/linkers can be added to alter the distance between the two structural components of the fusion protein, as well as alter the flexibility of this region.

In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilised metals (Porath J (1992) Protein Expr Purif 3-0.263281), protein A domains that allow purification on immobilised immunoglobulin, and the domain utilised in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and Fn14/TRAIL is useful to facilitate purification.

Additional fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

In another embodiment a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion proteins of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

The amino acid sequences of the present invention may be produced by expression of a nucleotide sequence coding for same in a suitable expression system.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for measuring the immunologic activity of any homolog, derivative or variant of any fusion protein of the present invention are well known in the art.

For example, any one of several conventional assays for monitoring cytokine production, as a measure of immune cells activation and differentiation, can be invoked. For example, for tracking T cell activation, interleukin-2 can be employed as a marker, which can be assayed as described in Proc. Natl. Acad. Sci. USA. 86:1333 (1989) the pertinent portions of which are incorporated herein by reference A kit for an assay for the production of interferon is also available from Genzyme Corporation (Cambridge, Mass.). One can also employ immunofluorescence and flow cytometry to monitor cytokine production on a cellular basis, and to monitor cell surface markers that reflect cellular activation and/or differentiation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Another assay for monitoring T cell proliferation is based on loading T cells with the CFSE dye, and subsequently monitoring by flow cytometry the dilution of this dye that accompanies successive cell divisions. In addition to monitoring the inhibition of T cell proliferation, the bioactivity of the fusion protein can also be monitored by evaluating its capacity to induce apoptosis in TRAIL receptor-positive tumor cell lines in which TRAIL receptor triggering leads to apoptosis. By combining these cells with other cells that have TWEAK on their surfaces, one can assess whether new fusion protein derivatives both anchor to TWEAK and thereby have their pro-apoptotic TRAIL-driven activity enhanced in this way.

Pharmaceutical Compositions and Dosing Regimens.

Administration of the compositions of this invention is typically parenteral, by intravenous, subcutaneous, intramuscular, or intraperitoneal injection, or by infusion or by any other acceptable systemic method. Administration by intravenous infusion, typically over a time course of about 1 to 5 hours, is preferred. In addition, there are a variety of oral delivery methods for administration of therapeutic proteins, and these can be applied to the therapeutic fusion proteins of this invention.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight.

Various modifications or derivatives of the fusion proteins, such as addition of polyethylene glycol chains (PEGylation), may be made to influence their pharmacokinetic and/or pharmacodynamic properties.

To administer the fusion protein by other than parenteral administration, it may be necessary to coat the protein with, or co-administer the protein with, a material to prevent its inactivation. For example, protein may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) J. Neuroimmunol. 7:27).

An "effective amount" of a composition of the invention is an amount that will ameliorate one or more of the well known parameters that characterize medical conditions caused by autoimmune diseases such as multiple sclerosis. Many such parameters and conditions have been described. An effective amount, in the context of multiple sclerosis, will be the amount of fusion protein that is sufficient to accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease. Clinically, this would result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically the treatment with fusion proteins of the present invention reduces one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

Although the compositions of this invention can be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. Remington's Pharmaceutical Science, 17$^{th}$ Ed. (Mack Publishing Company, Easton, Pa., 1990). Alternatively, compositions of the invention may be introduced into a patient's body by implantable drug delivery systems [Urquhart et al., Ann. Rev. Pharmacol. Toxicol. 24:199 (1984)].

Therapeutic formulations may be administered in many conventional dosage formulations. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), The Pharmacological Bases of Therapeutics, 8$^{th}$ Ed., Pergamon Press; and Remington's Pharmaceutical Sciences, supra, Easton, Pa.; Avis et al. (eds.) (1993) Pharmaceutical Dosage Forms Parenteral Medications Dekker, N.Y.; Lieberman et al. (eds.) (1990) Pharmaceutical Dosage Forms: Tablets Dekker, N.Y.; and Lieberman et al. (eds.) (1990), Pharmaceutical Dosage Forms: Disperse Systems Dekker, N.Y.

In additional embodiments, the present invention contemplates administration of the fusion proteins by gene therapy methods, e.g, administration of an isolated nucleic acid encoding a fusion protein of interest. The protein building blocks (e.g., first and second domains) of the fusion proteins of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, is also well within the ability of one skilled in the art. Administration of an isolated nucleic acid encoding the fusion protein is encompassed by the expression "administering a therapeutically effective amount of a fusion protein of the invention". Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., Circulation 97: 12, 1114-1123 (1998), and more recently, Fatham, C. G. 'A gene therapy approach to treatment of autoimmune diseases' Immun. Res. 18:15-26 (2007); and U.S. Pat. No. 7,378,089, both incorporated herein by reference. See also Bainbridge J W B et al. "Effect of gene therapy on visual function in Leber's congenital Amaurosis". N Engl J Med 358:2231-2239, 2008; and Maguire A M et al. "Safety and efficacy of gene transfer for Leber's Congenital Amaurosis". N Engl J Med 358:2240-8, 2008.

There are two major approaches for introducing a nucleic acid encoding the fusion protein (optionally contained in a vector) into a patient's cells; in vivo and ex vivo. For in vivo delivery the nucleic acid is injected directly into the patient, usually at the site where the fusion protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors (such as adenovirus, Herpes simplex I virus, adeno-associated virus), lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson et al., Science 256:808-813 (1992). See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. Fn14/TRAIL fusion proteins of the present invention can be delivered using gene therapy methods, for example locally in tumor beds, intrathecally, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the fusion proteins of the present invention, and then returning the transfected cells to the individual's body.

In some embodiments, the fusion proteins of the present invention are suitable for treatment of immune system diseases or disorders, including, but not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendo-crinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders).

In one embodiment, the fusion proteins of the present invention are used to treat multiple sclerosis.

In additional embodiments, the fusion proteins of the present invention can be used to treat various types of cancer. Soluble TRAIL has been associated with the induction of apoptosis in certain kinds of tumor cells. Moreover, for certain tumor types, inflammation may actually be pro-tumorigenic. Hence, a TRAIL fusion protein can be used to kill tumor cells directly, block pro-tumorigenic inflammation, and furthermore, can be used to block angiogenesis. The Fn14 component (the first domain) in this case would localize the TRAIL to TWEAK-positive cells (for example, on tumor endothelium and/or on tumor cells themselves).

The terms "cancer" and "cancerous" refer to or describe the physiological condition in mammals that is typically characterized by unregulated cell growth. As used herein, the term "patient" refers to a mammal, typically but not exclusively human, having cancer or other autoimmune disease and therefore in need of treatment by the methods of the present invention. The term "mammal in need of treatment" is used interchangeably with "patient".

Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia, chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

"Treating" or "treatment" or "alleviation" refers to both therapeutic treatment and prophylactic or preventative measures, wherein the object is to prevent or slow down (lessen) the targeted pathologic condition or disorder. A subject is successfully "treated" if, after receiving a therapeutic amount of a fusion protein of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient.

Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In a preferred embodiment, the cancer patients are still progression-free in the cancer after one year, preferably after 15 months. These parameters for assessing successful treatment and improvement in the disease are readily measurable by routine procedures familiar to a physician of appropriate skill in the art. The fusion proteins of the present invention are administered in amounts effective to provide improvement in any of the above parameters used to measure success in treatment of cancer, and can be readily determined by one skilled in the art. For example, an effective amount is that amount which is effective in inducing apoptosis in some cancer cells, or a majority of cancer cells, or substantially all of the patient's cancer cells. Other examples of an effective amount include amounts which are effective in reducing proliferation of tumour cells, of halting tumour progression via invasion of other tissues, reducing angiogenesis, and reducing inflammation.

In the context of treatment for cancer, the fusion proteins of the present invention can optionally be administered to a patient in combination with other chemotherapeutic agents. Suitable chemotherapeutic agents include, for example, alkylating agents such as thiotepa and cyclosphosphamide (CYTOXAN™; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins, capecitabine; and pharmaceutically acceptable salts, acids or derivatives of any of the above.

Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Also included in this definition are chemotherapeutic agents that are able to sensitize tumour cells to TRAIL and overcome TRAIL resistance, such as proteasome inhibitors and histone deacetylase (HDAC) inhibitors, cycloheximide, imatinib mesylate and other protein tyrosine kinase inhibitors, 17-allylamino-17-demethoxygeldanamycin, arsenic trioxide and X-linked Inhibitors of Apoptosis Protein small molecule antagonists; and pharmaceutically acceptable salts, acids or derivatives of any of these.

Additional information on the methods of cancer treatment is provided in U.S. Pat. No. 7,285,522, incorporated by reference in its entirety.

Accordingly, in a preferred embodiment, the fusion proteins of the present invention can be used to treat breast cancer. In another preferred embodiment, the fusion proteins of the invention can be used to treat colon cancer. In another embodiment, the fusion proteins of the invention can be used to treat liver cancer. In another preferred embodiment, the fusion proteins of the invention can be used to treat ovarian cancer. In another embodiment, the fusion proteins of the invention can be used to treat leukemia. In another embodiment, the fusion proteins of the invention can be used to treat melanoma. In further embodiments, the fusion proteins of the present invention can be used to treat alloimmune diseases, for example graft rejection, or graft-versus-host or host-versus-graft disease.

In further embodiments, the fusion proteins of the present invention can be used to modulate angiogenesis by administering an effective amount of the fusion protein, as described above. The use of TWEAK and other Fn14 agonists is described, for example, in U.S. Pat. No. 7,208,151, incorporated by reference herein in its entirety.

In the present invention, pro-inflammatory TWEAK signals, emanating from a range of TWEAK-bearing immune and non-immune cell types, are converted by Fn14-TRAIL into inhibitory TRAIL ones. Significantly, the opposing (anti-inflammatory TRAIL) neo-signals are by definition turning the TWEAK-bearing cell's attention, and in effect redirecting signaling, from Fn14$^+$TRAIL-R$^-$ to Fn14$^-$TRAIL-R$^+$ activated T cells driving autoimmune pathogenesis. The functional pleiotropism of the TWEAK:Fn14 and TRAIL:TRAIL-R signaling axes, especially the former, spanning an array of immune and non-immune cell types (Burkly L C, Michaelson J S, Hahm K, Jakubowski A, Zheng T S: TWEAKing tissue remodeling by a multifunctional cytokine: role of TWEAK/Fn14 pathway in health and disease, Cytokine 2007, 40:1-16; Winkles J A. The TWEAK-Fn14 cytokine-receptor axis: discovery, biology and therapeutic targeting, Nat Rev Drug Discov 2008; Zauli G, Secchiero P: The role of the TRAIL/TRAIL receptors system in hematopoiesis and endothelial cell biology, Cytokine Growth Factor Rev 2006, 17:245-257; Vince J E, Silke J: TWEAK shall inherit the earth, *Cell Death Differ* 2006, 13:1842-1844; Cretney E, Shanker A, Yagita H, Smyth M J, Sayers T J: TNF-related apoptosis-inducing ligand as a therapeutic agent in autoimmunity and cancer, Immunol Cell Biol 2006, 84:87-98), inheres in Fn14-TRAIL extensive functional possibilities for impacting and expanding cellular networking.

Unlike a simple TWEAK blocker (such as Fn14-IgG1 (mut)), the Fn14-TRAIL fusion protein substitutes anti-inflammatory TRAIL neo-signals for TWEAK pro-inflammatory signals. Thus, cells bearing surface TWEAK are in essence prevented from promoting TWEAK-driven inflammation and are instead redirected towards inhibiting TRAIL-R-bearing cells with which they might not otherwise interact (e.g., activated effector T cells). The impact of the TRAIL: TRAIL-R signaling axis on inflammatory events is largely via inhibition of a range of immune functions—T cell cycle progression, autoreactive T cell proliferation, pro-inflammatory cytokine production, Ab production, and inflammatory reactions. Hilliard B, Wilmen A, Seidel C, Liu T S, Goke R, Chen Y: Roles of TNF-related apoptosis-inducing ligand in experimental autoimmune encephalomyelitis, J Immunol 2001, 166:1314-1319; Lamhamedi-Cherradi S E, Zheng S, Tisch R M, Chen Y H: Critical roles of tumor necrosis factor-related apoptosis-inducing ligand in type 1 diabetes, Diabetes 2003, 52:2274-2278; Cretney E, McQualter J L, Kayagaki N, Yagita H, Bernard C C, Grewal I S, Ashkenazi A, Smyth M J: TNF-related apoptosis-inducing ligand (TRAIL)/Apo2L suppresses experimental autoimmune encephalomyelitis in mice, Immunol Cell Biol 2005, 83:511-519; Hirata S, Senju S, Matsuyoshi H, Fukuma D, Uemura Y, Nishimura Y; Prevention of experimental autoimmune encephalomyelitis by transfer of embryonic stem cell-derived dendritic cells expressing myelin oligodendrocyte glycoprotein peptide along with TRAIL or programmed death-1 ligand, J Immunol 2005, 174:1888-1897; Lamhamedi-Cherradi S E, Zheng S J, Maguschak K A, Peschon J, Chen Y H: Defective thymocyte apoptosis and accelerated autoimmune diseases in TRAIL−/− mice, Nat Immunol 2003, 4:255-260; Song K, Chen Y, Goke R, Wilmen A, Seidel C, Goke A, Hilliard B, Chen Y: Tumor necrosis factor-related apoptosis-inducing ligand (TRAIL) is an inhibitor of autoimmune inflammation and cell cycle progression, J Exp Med 2000, 191:1095-1104, Mi Q S, Ly D, Lamhamedi-Cherradi S E, Salojin K V, Zhou L, Grattan M, Meagher C, Zucker P, Chen Y H, Nagle J, Taub D, Delovitch T L: Blockade of tumor necrosis factor-related apoptosis-inducing ligand exacerbates type 1 diabetes in NOD mice, Diabetes 2003, 52:1967-1975. This range of immunoinhibitory effects clearly extends beyond $CD4^+$ T cells per se, encompassing $CD8^+$ T cells, B cells monocytes, and DC. Zauli G, Secchiero P: The role of the TRAIL/TRAIL receptors system in hematopoiesis and endothelial cell biology, Cytokine Growth Factor Rev 2006, 17:245-257, Kayagaki N, Yamaguchi N, Abe M, Hirose S, Shirai T, Okumura K, Yagita H: Suppression of antibody production by TNF-related apoptosis-inducing ligand (TRAIL), Cell Immunol 2002, 219: 82-91; Hayakawa Y, Screpanti V, Yagita H, Grandien A, Ljunggren H G, Smyth M J, Chambers B J: NK cell TRAIL eliminates immature dendritic cells in vivo and limits dendritic cell vaccination efficacy, J Immunol 2004, 172.123-129, Janssen E M, Droin N M, Lemmens E E, Pinkoski M J, Bensinger S J, Ehst B D, Griffith T S, Green D R, Schoenberger S P: CD4+ T-cell help controls CD8+ T-cell memory via TRAIL-mediated activation-induced cell death, Nature 2005, 434:88-93; You R I, Chang Y C, Chen P M, Wang W S, Hsu T L, Yang C Y, Lee C T, Hsieh S L: Apoptosis of dendritic cells induced by decoy receptor 3 (DcR3), Blood 2008, 111: 1480-1488. While there is evidence that TRAIL can induce apoptotic cell death in macrophages and neutrophils under certain conditions (Smyth M J, Takeda K, Hayakawa Y, Peschon J J, van den Brink M R, Yagita H: Nature's TRAIL—on a path to cancer immunotherapy, Immunity 2003, 18:1-6; Kaplan M J, Ray D, Mo R R, Yung R L, Richardson B C: TRAIL (Apo2 ligand) and TWEAK (Apo3 ligand) mediate CD4+ T cell killing of antigen-presenting macrophages, J Immunol 2000, 164:2897-2904; Renshaw S A, Parmar J S, Singleton V, Rowe S J, Dockrell D H, Dower S K, Bingle C D, Chilvers E R, Whyte M K: Acceleration of human neutrophil apoptosis by TRAIL, J Immunol 2003, 170:1027-1033), its pro-apoptotic activity is less clear for T cells. Lunemann J D, Waiczies S, Ehrlich S, Wendling U, Seeger B, Kamradt T, Zipp F: Death ligand TRAIL induces no apoptosis but inhibits activation of human (auto)antigen-specific T cells, J Immunol 2002, 168:4881-4888; Zhang X R, Zhang L Y, Devadas S, Li L, Keegan A D, Shi Y F: Reciprocal expression of TRAIL and CD95L in Th1 and Th2 cells: role of apoptosis in T helper subset differentiation, *Cell Death Differ* 2003, 10:203-210.

Chimerizing the Fn14 and TRAIL components within a single fusion protein may elicit special and sometimes complementary functional properties that could augment the efficacy of the two components, mask negative effects of one or the other which might otherwise limit their therapeutic utility, and confer special advantages. These include the following:

1) By linking Fn14, a protein that is naturally monomeric, to TRAIL (naturally a trimer), one is in effect creating a trimeric variant of Fn14. As it turns out, structural modeling suggests that this Fn14 neo-trimer could neatly dock with Fn14's naturally-trimeric TWEAK counter-receptor (FIG. 9). Moreover, the other end of the Fn14-TRAIL fusion protein, the trimeric TRAIL is docking with the trimeric DR5 receptor for TRAIL. Hence, these structural complementarities, generated de novo by chimerizing monomeric Fn14 to trimeric TRAIL, may actually be creating a uniquely stable TWEAK-Fn14-TRAIL-DR5 molecular bridge allowing for greater potency in blocking TWEAK and driving DR5 on cells facing each other. Furthermore, the modeling suggests that the chimera is rather rigid and thus might act like a spacer (of about 60 Å), limiting cell-to-cell contact locally between TWEAK-bearing cells and activated effector T cells. It is conceivable that local separation by 60 Å might interfere with other co-stimulatory molecules driving inflammatory responses, for example, within immune synapses.

2) TRAIL ligand is in effect being anchored to the cell surface via an Fn14 'bridge', which is in effect augmenting its effective valency. In a sense, this is replicating the situation with DC neo-expressing surface TRAIL, which have been shown to be effective in suppressing EAE. Hirata S, Senju S, Matsuyoshi H, Fukuma D, Uemura Y, Nishimura Y: Prevention of experimental autoimmune encephalomyelitis by transfer of embryonic stem cell-derived dendritic cells expressing myelin oligodendrocyte glycoprotein peptide along with TRAIL or programmed death-1 ligand, J Immunol 2005, 174:1888-1897.

3) TRAIL-mediated inhibition may function primarily at the EAE priming phase (during T cell triggering and expansion) (Cretney E, McQualter J L, Kayagaki N, Yagita H, Bernard C C, Grewal I S, Ashkenazi A, Smyth M J: TNF-related apoptosis-inducing ligand (TRAIL)/Apo2L suppresses experimental autoimmune encephalomyelitis in mice, Immunol Cell Biol 2005, 83:511-519), whereas TWEAK-blockade's benefit may be more focused on downstream pro-inflammatory events (including preventing breakdown of the blood brain barrier). Desplat-Jego S, Creidy R, Varriale S, Allaire N, Luo Y, Bernard D, Hahm K, Burkly L, Boucraut J: Anti-TWEAK monoclonal antibodies reduce immune cell infiltration in the central nervous system and severity of experimental autoimmune encephalomyelitis, Clin Immunol 2005, 117:15-23. Thus, by combining the two, one has a single agent that could in principle impact both priming and later phases of the disease.

4) TRAIL may contribute to death of neurons after the priming phase (Nitsch R, Pohi E E, Smorodchenko A, Infante-Duarte C, Aktas O, Zipp F: Direct impact of T cells on neurons revealed by two-photon microscopy in living brain tissue, J Neurosci 2004, 24:2458-2464, Aktas O, Smorodchenko A, Brocke S, Infante-Duarte C, Topphoff U S, Vogt J, Prozorovski T, Meier S, Osmanova V, Pohl E, Bechmann I, Nitsch R, Zipp F: Neuronal damage in autoimmune neuroinflammation mediated by the death ligand TRAIL, Neuron 2005, 46:421-432), in keeping with previous studies showing that both primary human neurons (Nitsch R, Bechmann I, Deisz R A, Haas D, Lehmann T N, Wendling U, Zipp F: Human brain-cell death induced by tumour-necrosis-factor-related apoptosis-inducing ligand (TRAIL), Lancet 2000, 356:827-828) and oligodendrocytes (Matysiak M, Jurewicz A, Jaskolski D, Selmaj K: TRAIL induces death of human oligodendrocytes isolated from adult brain, Brain 2002, 125: 2469-2480) are susceptible to TRAIL-induced cell death. By coupling Fn14 to TRAIL, one is providing an agent that sustains the integrity of the blood-brain barrier (via TWEAK blockade) and thereby mitigates TRAIL's access to the CNS. Moreover, since TWEAK has been reported to trigger neuronal cell death (Potrovita I, Zhang W, Burkly L, Hahm K, Lincecum J, Wang M Z, Maurer M H, Rossner M, Schneider A, Schwaninger M: Tumor necrosis factor-like weak inducer of apoptosis-induced neurodegeneration, J Neurosci 2004, 24:8237-8244), Fn14-TRAIL would be expected to protect neurons by blocking this TWEAK activity as well.

5) During EAE, the number of vessels correlates with both disease scores and pathological measures for inflammation, leukocyte infiltration and demyelination. Kirk S L, Karlik S J: VEGF and vascular changes in chronic neuroinflammation, J Autoimmun 2003, 21:353-363. Since TWEAK promotes angiogenesis (Jakubowski A, Browning B, Lukashev M, Sizing I, Thompson J S, Benjamin C D, Hsu Y M, Ambrose C, Zheng T S, Burkly L C: Dual role for TWEAK in angiogenic regulation, J Cell Sci 2002, 115:267-274) and TRAIL inhibits it (Cantarella G, Risuglia N, Dell'eva R, Lempereur L, Albini A, Pennisi G, Scoto G M, Noonan D N, Bernardini R: TRAIL inhibits angiogenesis stimulated by VEGF expression in human glioblastoma cells, Br J Cancer 2006, 94:1428-1435), Fn14-TRAIL may inhibit angiogenesis at inflammatory sites by a dual mechanism, that is, by antagonizing TWEAK's pro-angiogenic activity and synergistically reinforcing this effect through TRAIL's anti-angiogenic activity.

6) Yet another synergy could stem from modulation of endothelial cell function and chemokine expression. As stated above, blockade of TWEAK may interfere with chemokine expression by, and leukocyte adhesion to, endothelial cells. TRAIL is also linked to these processes. TRAIL counteracts TNF-α-induced leukocyte adhesion to endothelial cells by down-modulating CCL8 and CXCL10 chemokine expression and release. Secchiero P, Corallini F, di Iasio M G, Gonelli A, Barbarotto E, Zauli G: TRAIL counteracts the proadhesive activity of inflammatory cytokines in endothelial cells by down-modulating CCL8 and CXCL10 chemokine expression and release, Blood 2005, 105:3413-3419. Thus, Fn14-TRAIL could impact leukocyte attraction and adhesion through both its Fn14 and TRAIL ends.

EXAMPLES

The following examples are intended to illustrate the invention and should not be construed as limiting the invention in any way.

Materials and Methods

Mice 4-6 week old C57BL/6 female mice were purchased from the Jackson Laboratory (Bar Harbor, Me.), and were maintained under pathogen-free conditions at the University of Pennsylvania Animal Facility. All animal experiments were approved by the University of Pennsylvania Animal Care and Use Committee.

Reagents

Plasmids pT2/BH and pNEB193 UbC-SB11 were provided by Dr. Perry Hacket (University of Minnesota, Minneapolis), and murine TRAIL and TWEAK cDNAs were obtained from Dr. Hideo Yagita (Juntendo University School of Medicine, Tokyo, Japan). The plasmid pMFneo was obtained from Dr. Herman Waldmann (University of Oxford, Oxford, UK). Mouse MOG 38-50 peptide (GWYRSPFSRVVHL (SEQ ID NO: 3)) was synthesized using F-moc solid phase methods and purified by HPLC at Invitrogen Life Technologies (Carlsbad, Calif.). Pertussis toxin was purchased from EMD Biosciences (San Diego, Calif.). The following reagents were purchased from BD Pharmingen (San Diego, Calif.): ELISA Ab pairs for mouse IL-2, IL-4, IL-6, IFN-γ and recombinant mouse IL-2, IL-4, IL-6, IFN-γ. An IL-17 ELISA Ab pairs was obtained from Southern Biotech (Alabama, USA), and recombinant mouse IL-17 was purchased from Biosource (Camarillo, Calif.). PE-anti-mouse TRAIL and PE-anti-mouse TWEAK were purchased from eBioscience (San Diego, Calif.). Recombinant TRAIL (Super Killer TRAIL™) was purchased from Axxora Platform (San Diego, Calif.).

Plasmid Construction

Chimeric Fn14-TRAIL and Fn14-IgG1(mut) coding cassettes were constructed by PCR, using partially overlapping synthetic oligonucleotides. cDNA encoding amino acids (aa) 1-79 of murine Fn14 (Swiss-prot accession number Q9CR75) was joined to cDNA encoding either aa 118-291 of murine TRAIL (Swiss-prot accession number P50592) or a mutated human IgG1 Fc ($Fc_{\gamma 1}$) segment, respectively. For the latter, a cDNA encoding human $Fc_{\gamma 1}$ (Brunschwig E B, Levine E, Trefzer U, Tykocinski M L: Glycosylphosphatidylinositol-modified murine B7-1 and B7-2 retain costimulator function, J Immunol 1995, 155:5498-5505) was modified by PCR-based site-directed mutagenesis, using oligonucleotides configured to mutate C220→S, C226→S, C229→S, N297→A, E233→P, L234→V, and L235→A. To express soluble TRAIL, cDNA encoding aa 118-291 of murine TRAIL was used. All of these cDNA segments were subcloned into a pMFneo eukaryotic expression vector downstream of an EF1α promoter region. Coding sequence for luciferase was mobilized with Hind3- and BamH1 from pTAL-Luc (BD Biosciences; San Jose, Calif.), and subcloned into the respective sites of pMFneo. cDNA encoding full length murine TWEAK was generated by PCR and subcloned into the pcDNA3 eukaryotic expression vector (Invitrogen Life Technologies, Carlsbad, Calif.).

To generate a derivative Sleeping Beauty expression vector incorporating within the same plasmid both transposon and transposase cassettes, a transposase coding sequence flanked upstream by a ubiquitin C promoter was generated by PCR from pNEB193 UbC-SB11 (b.p. 432-2958) and then ligated between the Apa1 and Xho1 sites of pT2/BH vector, which contains a transposon cassette. This new expression vector, incorporating both transposase and transposon expression cassettes, was designated pSBC21. Next, cDNAs corresponding to Fn14-TRAIL, soluble Fn14, Fn14-IgG1(mut), soluble TRAIL, or luciferase, each linked to the EF1α promoter, were subcloned from their respective pMFneo expression constructs into the transposon cassette of pSBC21, downstream of the transposase expression module. All subcloned cDNAs were oriented in the same direction as the transposase.

Cell Culture and Transfection

Human 293 kidney cells and CHO cells were cultured in DMEM and HAM'S F-12, respectively, supplemented with 100 μg/ml penicillin, 100 U/ml streptomycin, 2 and 10% heat-inactivated fetal bovine serum. 293 cells were transiently transfected with the Fn14-TRAIL, soluble Fn14, Fn14-IgG1(mut) and soluble TRAIL pMFneo expression plasmids, using LipofectAMINE™ reagent (Invitrogen Life Technologies, Carlsbad, Calif.) Proteins in conditioned media were resolved by SDS-PAGE and detected by Western blot analysis. Anti-mouse Ab used for detecting Fn14 and TRAIL were purchased from eBioscience and R&D (Minneapolis, Minn.), respectively. CHO cells were transiently transfected with a pcDNA3-based murine TWEAK expression construct. TWEAK expression on transfectants was verified by immunofluorescence and flow cytometry.

Induction and Disease Evaluation of EAE

EAE was induced according to a standard induction protocol. Stromnes I M, Goverman J M: Active induction of experimental allergic encephalomyelitis, Nat Protoc 2006, 1:1810-1819. Briefly, female C57BL/6 mice were challenged with a total of 300 μg of $MOG_{38-50}$ peptide (divided into two subcutaneous injections, one on each dorsal flank) in 0.1 ml PBS, emulsified in an equal volume of CFA containing 4 mg/ml *Mycobacterium tuberculosis* H37RA (Difco, Detroit, Mich.). These mice were simultaneously injected intravenously with 100 ng of pertussis toxin in 0.2 ml PBS. A second intravenous injection of pertussis toxin (100 ng/mouse) was given 48 h later. Mice were examined daily for signs of EAE and scored as follows: 0, no disease; 1, tail paralysis; 2, hind limb weakness; 3, hind limb paralysis; 4, hind limb plus forelimb paralysis; 5, moribund or dead.

Cytokine and Proliferation Assays

For cytokine assays, splenocytes were cultured at $1.5 \times 10^6$ cells per well in 0.2 ml of DMEM with 10% FBS, in the presence or absence of different concentrations of $MOG_{38-50}$ peptide, or 1 μg/ml Con A (Sigma-Aldrich, St. Louis, Mo.). Conditioned media were collected 40 h later, and cytokine concentrations were determined by quantitative ELISA, using paired mAb specific for the corresponding cytokines, per the manufacturer's recommendations (BD Pharmingen, (San Diego, Calif.). Proliferation assays were performed using $0.5 \times 10^6$ cells per well in 96-well plates. [$^3$H] thymidine was added to the cultures at 48 h, and cells were harvested 16 h later. Radioactivity was determined using a flatbed β-counter (Wallac).

Hydrodynamic Injection

Mice were injected with pSBC21 vector alone or pSBC21-based expression constructs incorporating Fn14-TRAIL, soluble Fn14, Fn14-IgG1(mut), soluble TRAIL, or luciferase coding sequences. Expression plasmids were dissolved in saline in a volume (in ml) equivalent to 10% of body weight (in gm). The entire volume for each animal was injected within 5 sec via tail veins, according to a published protocol. Liu F, Song Y, Liu D: Hydrodynamics-based transfection in animals by systemic administration of plasmid DNA, Gene Ther 1999, 6:1258-1266. Retro-orbital blood samples were collected using heparinized glass capillaries. After centrifugation, plasma was recovered and kept at −20° C. until ELISA assays were performed.

Measurement of Recombinant Proteins in Serum

ELISA assays were performed in 96-well microtitration plates. For Fn14-TRAIL, soluble Fn14, and Fn14-IgG1(mut), purified anti-human/mouse Fn14/TWEAK receptor Ab from eBioscience (San Diego, Calif.) was used as capture Ab; for soluble TRAIL, anti-mouse TRAIL Ab from R&D Systems (Minneapolis, Minn.) was used as capture Ab. Detecting Ab were: biotin-anti-mouse TWEAK receptor Ab from eBioscience for Fn14; biotin-anti-mouse TRAIL Ab from eBioscience for Fn14-TRAIL and soluble TRAIL; anti-human IgG, Fcγ fragment-specific Ab from Jackson ImmunoResearch Laboratories (West Grove, Pa.) for Fn14-IgG1 (mut).

Capture Ab diluted in coating buffer (0.1 M carbonate, pH 8.2) was distributed in microtitration plates and incubated at 4° C. overnight. After washing twice with 0.05% Tween-20 in PBS, wells were incubated for an additional 2 h at RT with PBS-3% albumin to block nonspecific binding sites. After washing twice again, 100 μl of serum samples were added and incubated at 4° C. overnight. After incubation, wells were rinsed four times and incubated for 1 h with biotinylated detection Ab. For the enzymatic reaction, avidin peroxidase and TMB Microwell peroxidase substrate (KPL, Gaithersburg, Md.) were applied sequentially.

In Vivo Bioluminescence Imaging

All the imaging work was performed at the Small Animal Imaging Facility (SAIF) in the Department of Radiology at the University of Pennsylvania. Images were acquired at 5 h, 24 h, 5 days, 22 days, 34 days, 51 days, and 1 year after injection of the luciferase expression plasmid. At the time of imaging, mice were anesthetized with ketamine/xylazine. D-luciferin (Biotium, Hayward, Calif.) was dissolved in saline and delivered via intraperitoneal injection before imaging. Mice were then placed in an imaging chamber in which the temperature was maintained at 33° C. Bioluminescent images were acquired using the Xenogen in vivo Imaging System (IVIS; Xenogen Corp, Alameda, Calif.). Imaging parameters were field of view of 8 or 10 cm, exposure time of 4 minutes, number of binning 16, and f1/stop of 1. For display, the luminescent image (pseudocolor) was overlaid on a photographic image, which delineated the anatomic landmarks.

Measurement of Blood-Brain Barrier (BBB) Permeability

BBB permeability was assessed essentially as described (Prasad R, Giri S, Nath N, Singh I, Singh A K: 5-aminoimidazole-4-carboxamide-1-beta-4-ribofuranoside attenuates experimental autoimmune encephalomyelitis via modulation of endothelial-monocyte interaction, J Neurosci Res 2006, 84:614-625), with some modifications. Briefly, on days 6 and 13 after MOG challenge, 4% Evans blue dye (Sigma-Aldrich, St. Louis, Mo.) was injected into the tail veins of C57BL/6 mice. After 1 h, animals were anesthetized and transcardially perfused with saline to remove intravascular dye. Following euthanasia, spinal cords, cerebellums/brainstems and brains were collected. For quantitative measurements, spinal cords were homogenized in 1 ml PBS. Samples were centrifuged once at 15,800 g for 30 min. 600 μl aliquots of the supernatant were then collected and added to 600 ul of 100% TCA (Sigma Aldrich St. Louis, Mo.). This solution was incubated overnight, and centrifuged at 15,800 g for 30 min. Evans blue extravasation was quantified spectrophotometrically (excitation 630 nm and emission 680 nm) in the supernatants.

Preparation and Analysis of Infiltrating Cells from Spinal Cords

Single cell suspensions of spinal cords were prepared as described previously. Hilliard B, Samoilova E B, Liu T S, Rostami A, Chen Y: Experimental autoimmune encephalomyelitis in NF-kappa B-deficient mice:roles of NF-kappa B in the activation and differentiation of autoreactive T cells, J Immunol 1999, 163:2937-2943. Briefly, mice were sacrificed and spinal cords were removed, placed in ice-cold RPMI medium containing 27% Percoll, and pressed through a 70-µm Falcon cell strainer. The resulting cell suspension was brought to a volume of 50 ml with additional 27% Percoll, mixed, and centrifuged at 300×g for 15 min. The pellet was kept on ice, while the myelin layer and supernatant were transferred to a new 50-ml tube, homogenized by shaking, and centrifuged again at 300×g for 15 min. The cell pellets were then combined and washed three times in RPMI medium at 4° C. For flow cytometric analysis, single cell suspensions of recovered cells were incubated for 45 min with the following Ab: FITC-anti-mouse-IFNγ, PE-anti-mouse IL-10, APC-anti-mouse IL-17, APC-Alexa flour 750-anti-mouse CD4, Percp-cy5.5-anti-mouse CD8, and PE-cy7-anti-mouse CD69, all purchased from eBioscience.

Molecular Modeling of the Chimeric Fn14-TRAIL Protein

A three-dimensional model of the Fn14-TRAIL protein was generated using the crystal structure of TRAIL (pdb code: 1D0G) (Hymowitz S G, Christinger H W, Fuh G, Ultsch M, O'Connell M, Kelley R F, Ashkenazi A, de Vos A M: Triggering cell death: the crystal structure of Apo2L/TRAIL in a complex with death receptor 5, Mol Cell 1999, 4:563-571) and a modeled Fn14 molecule. A three-dimensional model of the ligand binding domain (LBD) of Fn14 was generated using MODELLER. Marti-Renom M A, Stuart A C, Fiser A, Sanchez R, Melo F, Sali A: Comparative protein structure modeling of genes and genomes, Annu Rev Biophys Biomol Struct 2000, 29:291-325. Briefly, the starting model of the LBD of Fn14 was obtained based on the template structure of human TACI (1XU1) and BCMA (1XU2). Hymowitz S G, Patel D R, Wallweber H J, Runyon S, Yan M, Yin J, Shriver S K, Gordon N C, Pan B, Skelton N J, Kelley R F, Starovasnik M A: Structures of APRIL-receptor complexes: like BCMA, TACI employs only a single cysteine-rich domain for high affinity ligand binding, J Biol Chem 2005, 280:7218-7227. The extended region of Fn14 was treated as a linker between Fn14 and TRAIL. To obtain a stereochemically and energetically favored model, the linker conformation was optimized by short molecular simulation studies using InsightII (Accelrys, Inc. San Diego, Calif.) as described before. Swaminathan P, Hariharan M, Murali R, Singh C U: Molecular structure, conformational analysis, and structure-activity studies of Dendrotoxin and its homologues using molecular mechanics and molecular dynamics techniques, J Med Chem 1996, 39:2141-2155.

Flow Cytometry and MTT Assays

Immunostaining was performed at 4° C. with specified Ab suspended in PBS containing 0.5% BSA and 0.05% sodium azide ($NaN_3$). All flow cytometric analyses were performed on a FACS Calibur apparatus with Cell Quest software and dual laser (488 and 633 nm) excitation (BD Biosciences). The MTT assay was performed according to the manufacturer's protocol (ATCC, Manassas, Va.).

Statistical Analysis

The Student's t test or Mann-Whitney U test was used to determine the statistical significance of differences. A p value of <0.05 was considered to be statistically significant.

Results

Production of Functional Fn14-TRAIL Protein

Figure 1:
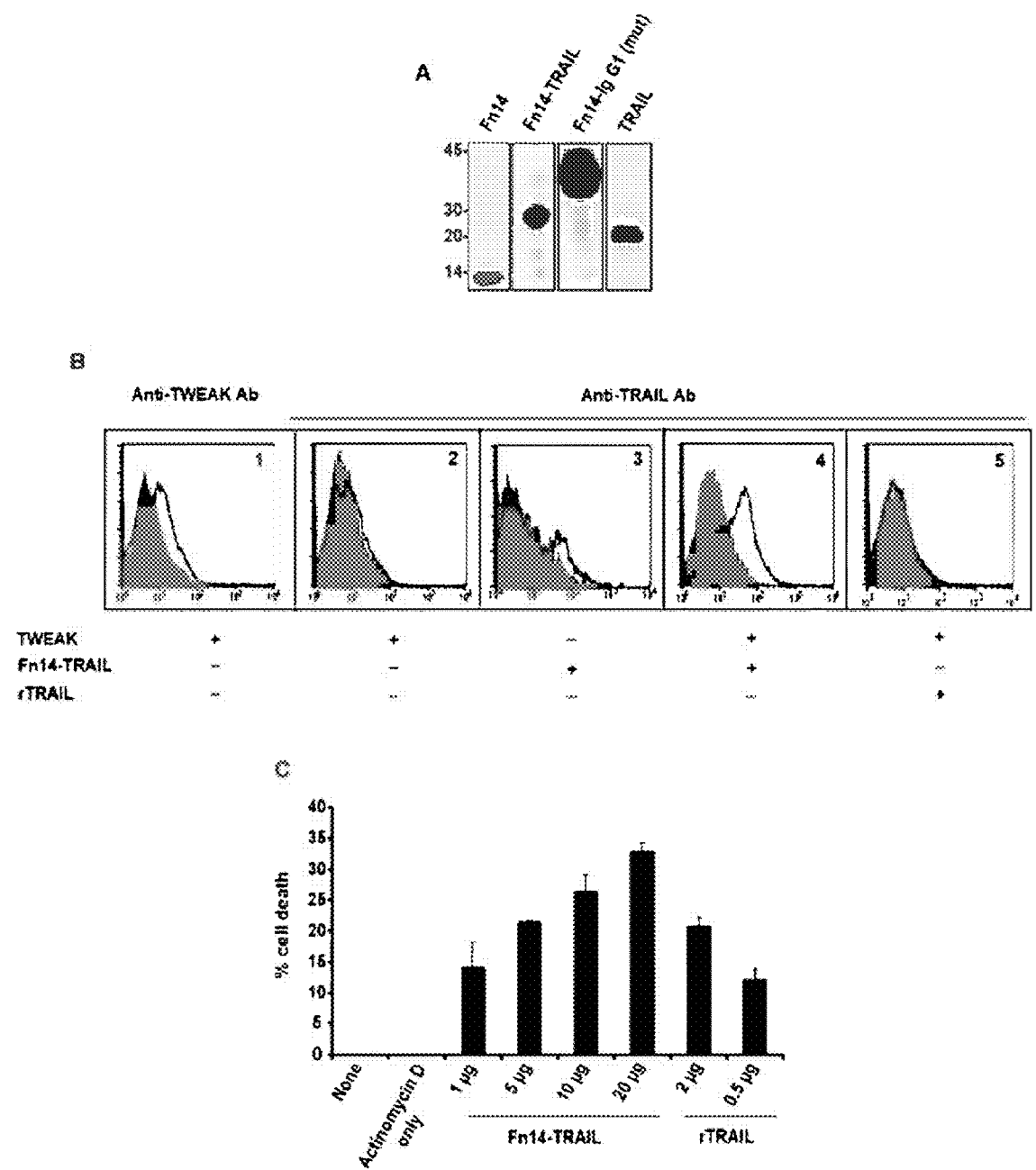
FIG. 1. Expression and functional analysis of Fn14-TRAIL

Recombinant Fn14-TRAIL, along with related control proteins (soluble Fn14, Fn14-IgG1(mut), soluble TRAIL), were produced using a pMFneo eukaryotic expression system. The chimeric Fn14-TRAIL coding sequence linked the full extracellular domains of the Fn14 type I and TRAIL type II membrane proteins, thereby creating a hybrid soluble type I-type II fusion protein. To generate the Fn14-IgG1(mut) coding sequence, several amino acids within the human IgG1 component were mutated (see Material and Methods) in order to block FcγR binding (and consequent non-specific depletion of lymphocytes) and to interfere with N-glycosylation (which is important for in vivo effector function of human IgG1). Isaacs J D, Greenwood J, Waldmann H: Therapy with monoclonal antibodies. II. The contribution of Fc gamma receptor binding and the influence of C(H) 1 and $C(H)_3$ domains on in vivo effector function, J Immunol 1998, 161: 3862-3869. The various pMFneo-based expression constructs were transiently transfected into 293 cells, and expression and secretion of the respective proteins was demonstrated by Western blot analysis of conditioned media (FIG. 1A).

To validate the identity of expressed Fn14-TRAIL, its ability to bind to Fn14's ligand, TWEAK, was assessed. To this end, CHO cells were transiently transfected with a murine TWEAK cDNA expression construct (in the pcDNA3 vector), and after 48 h, transfectants were incubated at 4° C. with purified Fn14-TRAIL or soluble TRAIL. Immunofluorescence and flow cytometric analysis of these cells, using anti-mouse TWEAK and anti-mouse TRAIL as detecting Ab, showed significant binding of Fn14-TRAIL, but not soluble TRAIL, to cell surface TWEAK on transfectants (FIG. 1B).

The functionality of the TRAIL component of Fn14-TRAIL was determined by evaluating its capacity to induce apoptosis in L929 cells, using an MTT assay. As shown in FIG. 1C, Fn14-TRAIL induces apoptosis of L929 cells in a dose-dependent manner in the presence of actinomycin D. Recombinant TRAIL (Super Killer TRAIL™) was used as a positive control in this experiment. Of note, no TWEAK was detected by immunofluorescence and flow cytometry on these L929 cells (not shown), arguing against the possibility that the Fn14 component of Fn14-TRAIL drives apoptosis through some kind of back-signaling through surface TWEAK.

Development of a Transposon-Based Expression System for Sustained In Vivo Expression of Fn14-TRAIL To enable sustained in vivo expression of Fn14-TRAIL (and control proteins), the transposon-based 'Sleeping Beauty (SB)' expression system was invoked. This system combines the advantages of plasmid-mediated gene delivery together with an ability to integrate into the chromosome and provide for sustained transgene expression. To optimize the efficiency of this expression system, a derivative expression vector was generated, designated pSBC21, that combines within a single plasmid both transposon (accommodating the transgene of interest) and transposase expression cassettes (FIG. 2A). Since the relative expression level from the two cassettes is important, a number of promoter combinations were screened, and determined that a combination of UBC promoter (driving the transposase) and EF1α promoter (driving the transposon cassette), arrayed in tandem, affords strong transgene expression (not shown).

The functionality of this unique dual-cassette transposon/transposase vector derivative (with a UBC/EF1α promoter combination) was validated using a luciferase reporter. A pLuciferase•SBC21 plasmid, at varying concentrations, was administered by hydrodynamic injection to C57BL/6 mice. Hydrodynamic injection of transposon-based expression constructs provides for sustained gene expression in mouse hepatocytes in vivo. Liu F, Song Y, Liu D: Hydrodynamics-based transfection in animals by systemic administration of plasmid DNA, Gene Ther 1999, 6:1258-1266. Bioluminescent images acquired after administration of luciferase's substrate, D-Luciferin, revealed luciferase expression at 22 days (FIG. 2B), with significant levels still detected after six months (not shown).

Having documented the functionality of the derivative expression vector using a luciferase reporter, this vector was invoked for expressing Fn14-TRAIL, specifically asking whether levels of Fn14-TRAIL in serum correlate with the dose of injected pFn14-TRAIL•SBC21 plasmid. C57BL/6 mice (in experimental groups of four) were each treated with a single hydrodynamic injection of pFn14-TRAIL•SBC21 plasmid, in escalating doses (5, 10 or 20 µg of plasmid). Serum levels of Fn14-TRAIL were measured by ELISA twenty days after plasmid administration, and a dose-dependent increase in serum Fn14-TRAIL levels was observed, starting with the 10 µg plasmid dose (FIG. 2C).

Fn14-TRAIL Suppresses MOG-Induced Autoimmune Encephalomyelitis

The therapeutic potential of Fn14-TRAIL in a murine EAE disease model was investigated next. To this end, a single encephalitogenic dose of $MOG_{35-50}$ peptide was administered to C57BL/6 mice. Two days after peptide injection, a single dose of pFn14-TRAIL•SBC21 plasmid (50 µg/mouse), or one of four control plasmids (pFn14•SBC21, pFn14-IgG1(mut)•SBC21, pTRAIL•SBC21, and pSBC21) was administered by hydrodynamic injection. By ELISA, comparable serum levels of expressed proteins in animals hydrodynamically-injected with each of the respective plasmids (FIG. 3A) were detected. Disease progression in the treated mice was monitored by both physical examination and histological analysis of recovered spinal cords. Fn14-TRAIL expression significantly attenuated EAE manifestations, with decreases in both mean clinical scores (calculated over a 43-day period post-MOG administration; FIG. 3B, upper panel) and cumulative mean clinical score (calculated over a 40-day period post-MOG administration; Table 1 and FIG. 3C). Mean maximum disease score was also significantly lower in the Fn14-TRAIL-treated group, as compared to the various controls (Table 1). Similarly, the disease score at day 35 was also significantly lower for the Fn14-TRAIL group (Table 1; FIG. 3D).

Fn14-TRAIL's therapeutic benefit was also evident from an analysis of day of disease onset and disease incidence. Fn14-TRAIL extended the mean day of disease onset (14.8±4.7 days), compared to control mice treated with empty vector (12.8±4 days), and typically the latter mice developed EAE starting at ~10 days post-MOG peptide administration (Table 1). The mean day of disease onset for mice receiving pFn14•SBC21, pFn14-IgG1(mut)•SBC21, pTRAIL•pSBC21 plasmids were 13.63±2.72, 11.66±1.2 and 13.42±2.2 days, respectively. Although all expressed proteins reduced disease incidence to some extent, only 50% of Fn14-TRAIL-treated animals showed signs of the disease (FIG. 3B, lower panel) during the course of this experiment.

Fn14-TRAIL is More Effective than its Component Parts, in Combination

Having shown that neither of the components of Fn14-TRAIL, when administered as soluble agents one at a time, are as effective as Fn14-TRAIL in suppressing EAE, the question of whether the Fn14-TRAIL fusion protein's therapeutic efficacy can be recapitulated by administering soluble Fn14 and TRAIL proteins simultaneously was evaluated, using the same EAE model. Two days after administering a single encephalitogenic challenge of $MOG_{38-50}$ peptide to C57BL/6 mice, single doses of either pFn14-TRAIL•SBC21 plasmid (25 µg/mouse) or a mixture of pFn14•SBC21 and pTRAIL•SBC21 plasmids (25 µg each/mouse) were hydrodynamically injected into the animals. While Fn14-TRAIL significantly suppressed EAE as before, with decreases in both mean clinical scores (FIGS. 4A and 4B) and cumulative mean clinical score (FIG. 4C), the combination of soluble Fn14 and soluble TRAIL showed no significant therapeutic effect. Serum levels of these various proteins, expressed by hydrodynamic injection of the respective transposon-based expression plasmids, were comparable, as measured by ELISA (FIG. 4D). Taken together, these data establish that Fn14-TRAIL has substantial therapeutic benefit in preventing EAE induction, and this effect cannot be replicated by simply administering this fusion protein's two component elements as soluble agents in combination.

Fn14-TRAIL Blocks Proliferation and Differentiation of Autoreactive T Cells

Fn14-TRAIL's effect on the proliferation and differentiation of myelin-specific T cells recovered from treated animals was assessed. To this end, splenocytes were recovered 43 days after MOG challenge from both Fn14-TRAIL-treated and control mice receiving vector only. These splenocytes were evaluated in vitro for their proliferation and cytokine production in response to $MOG_{38-50}$ peptide. Splenocytes from control animals proliferated vigorously in response to MOG peptide (FIG. 4E) and produced significant amounts of Th1 (IL-2 and IFN-γ), Th2 (IL-10, IL-4 and IL-6) and Th17 (IL-17) cytokines (FIG. 5). By contrast, splenocytes from Fn14-TRAIL-treated animals proliferated to a lesser extent in response to MOG stimulation (FIG. 4E) and produced significantly less of these various cytokines (FIG. 5). Taken together, these results indicate that both T cell proliferation and the expression of an array of T cell cytokines are attenuated by in vivo treatment with Fn14-TRAIL.

Fn14-TRAIL Reduces Infiltration of Inflammatory Cells into CNS

A key pathologic feature of EAE is infiltration of inflammatory cells into the CNS. Fn14-TRAIL's effect on this infiltrative process was assessed. To this end, a comparison of the absolute number of inflammatory cells, along with the percentage of early activated $CD4^+$ and $CD8^+$ cells and of IFNγ-, IL-17- and IL-10-expressing cells, in the spinal cords of Fn14-TRAIL-versus vector-treated EAE mice on days 7 and 14 post-MOG challenge was made. On day 7, all these parameters were markedly reduced in the Fn14-TRAIL-treated group (FIGS. 6A-D). At day 14 (peak of the disease), the Fn14-TRAIL-associated reduction in absolute numbers of cytokine-expressing cells was still manifest (FIGS. 6E-F).

These findings with inflammatory cells recovered from spinal cords were consistent with histopathological examination of spinal cord tissues recovered 43 days post-MOG challenge. Whereas control vector-only treated animals uniformly displayed multiple inflammatory foci within their spinal cords, Fn14-TRAIL-treated mice exhibited a dramatic reduction of inflammatory cell infiltration in their spinal cords (FIGS. 7A-B).

Fn14-TRAIL Attenuates Blood-Brain Barrier Permeability

TWEAK is known to increase the permeability of the neurovascular membrane unit, by inducing MMP-9 (metalloproteinase-9) expression. Polavarapu R, Gongora M C, Winkles J A, Yepes M: Tumor necrosis factor-like weak inducer of apoptosis increases the permeability of the neurovascular unit through nuclear factor-kappa B pathway activation, J Neurosci 2005, 25:10094-10100. The decreased infiltration of inflammatory cells into the CNS seen in Fn14-TRAIL-treated mice could be a consequence, at least in part, of a reduction in TWEAK-dependent enhancement of blood brain barrier (BBB) permeability. BBB integrity was evaluated by a conventional approach, according to which CNS penetration of intravenously introduced Evans blue dye is monitored Prasad R, Giri S, Nath N, Singh I, Singh A K: 5-aminoimidazole-4-carboxamide-1-beta-4-ribofuranoside attenuates experimental autoimmune encephalomyelitis via modulation of endothelial-monocyte interaction, J Neurosci Res 2006, 84:614-625. Evans blue in the CNS of EAE mice was measured before (6 days post-MOG administration) or during (13 days post-MOG administration) the peak of the disease. Dye was quantitated in homogenates of various dissected CNS structures. Whereas there was no significant difference in detectable dye between brains of control vector-only and Fn14-TRAIL-treated animals at either time-point (FIGS. 8A and 8B), significantly more dye was detected for the vector-only treated animals in the other CNS structures (spinal cord and cerebellum/brain stem) at both days 6 (FIG. 8A) and 13 (FIG. 8B).

The concentration of dye penetrated into the spinal cords was correlated with the respective EAE mean clinical scores on the day of dye application. Significantly, even for mice with the same EAE mean clinical scores (0 or 1) on day 13, control vector-only-treated mice showed higher concentrations of dye in their spinal cords compared to Fn14-TRAIL-treated mice (FIG. 8C). This finding, coupled with the findings of reduced inflammatory cell infiltration in Fn14-TRAIL-treated spinal cords, provides evidence that Fn14-TRAIL attenuates infiltration of inflammatory cells across the endothelial BBB by suppressing the progressive increase in BBB permeability that accompanies encephalomyelitis.

Molecular Model of the Chimeric Fn14-TRAIL Protein

The question of whether Fn14-TRAIL's significant therapeutic efficacy might stem, at least in part, from the way in which it engages and bridges TWEAK ligand and TRAIL receptor (DR5) molecules, was assessed. To this end, the Fn14-TRAIL protein was modeled, both as a monomer (FIG. 9A) and as a trimer (FIG. 9B-C). The putative interaction of trimeric Fn14-TRAIL at its opposite ends with TWEAK and DR5, respectively, was also visualized (FIG. 9D). Significantly, the modeled TWEAK:Fn14-TRAIL:DR5 complex showed that: (1) the TWEAK-binding domains of Fn14, when forced into an artificial 'trimeric' configuration by the chimerized, naturally-trimeric TRAIL component, are favorably positioned to interact with their cognate partners within trimeric TWEAK; (2) the DR5-binding domains of trimeric TRAIL are favorably positioned to interact with their cognate partners within trimeric DR5; and (3) the carboxy-terminus of the Fn14 component within the fusion protein serves as a surrogate 'linker' that is sufficiently rigid to keep the Fn14 and TRAIL domains apart, with no propensity for collapsing. Interestingly, the ligand binding domains of Fn14 and TRAIL are separated by about 60 Å, raising the possibility that this fusion protein could act like a spacer between the interacting cells and limit local cell-to-cell contact. Taken together, the modeling analysis verified that the Fn14-TRAIL chimera can indeed simultaneously engage both TWEAK and DR5 on opposing cells. Moreover, the enforced Fn14 'neo-trimer' assumes a configuration that allows for binding to the natural TWEAK trimer, perhaps creating a particularly stable higher order structure.

TABLE 1

Clinical features of EAE.

| treatment groups | day of onset (mean ± SD)* | maximum clinical score (mean ± SEM) | score at day 35 (mean ± SEM) | cumulative score (mean ± SEM)** |
|---|---|---|---|---|
| Vector (n = 8) | 12.80 ± 4.18 | 2.44 ± 0.359 | 1.933 ± 0.29 | 48.00 ± 9.78 |
| Fn14 (n = 8) | 13.62 ± 2.72 | 2.22 ± 0.383 | 1.750 ± 0.54 | 44.00 ± 12.52 |
| Fn14-TRAIL (n = 9) | 14.80 ± 4.7 | 1.22 ± 0.465 | 0.611 ± 0.261 | 18.60 ± 7.45 |
| Fn14-IgG (mut) (n = 9) | 11.66 ± 1.2 | 2.80 ± 0.286 | 1.944 ± 0.306 | 60.05 ± 7.44 |
| TRAIL (n = 8) | 13.42 ± 2.2 | 1.81 ± 0.472 | 1.438 ± 0.448 | 42.06 ± 11.08 |

*Day of onset is the first day after immunization when mice showed signs of EAE (only mice that developed EAE were included).
**Cumulative score is the sum of clinical score of each mouse.

Production and Purification of the Human Fn14-TRAIL Protein

Clone Construction

The expression cassette used to produce human Fn14-TRAIL was comprised of coding sequence for the human urokinase signal peptide followed by coding sequence for human Fn14-TRAIL. The coding sequences were codon-optimized for enhanced expression in Chinese Hamster Ovary (CHO) cell-lines. The DNA coding sequence were synthesized and then sub-cloned into a mammalian expression vector designed for chromosomal integration and optimized for high level expression in CHO cells.

The Fn14-TRAIL expression vector was transfected into CHO-S cells, and a clone pool was isolated for initial expression analysis. Out of this clone pool, a single high-producing clone was isolated, and expression of the Fn14-TRAIL protein was analyzed by various methods such as ELISA, SDS-PAGE and Western Blots (see FIG. 10). Production levels were optimized to reach expression of approximately 100 mg of Fn14-TRAIL per liter of fermentation media.

Western blot analysis was performed for shake flask culture medium samples obtained from the Fn14-TRAIL clone grown in various media formulations (shown in the various lanes). The Western blot was probed using a commercial anti-human TRAIL/TNFSF10 Ab as primary detecting antibody. The calculated molecular weight of Fn14-TRAIL is 24.6 kD.

A high-yield, multi-step chromatographic purification process was developed, which included an efficient capture step, an anion-exchange chromatography step, and then a final buffer exchange step, the latter carrying the product into the formulation buffer. This purification process allows for the isolation of highly-purified Fn14-TRAIL protein. Western Blot analysis of sample taken from the last stage of purification (corresponding to FIG. 11, far right lane) showed that the purified protein is primarily a monomer and partially a homodimer (not shown). The small amount of degradation product seen on the SDS-PAGE gel was not detected by the Fn14-specific Ab, but was detected with the TRAIL-specific Ab.

A seven-liter production fermentation followed by the above purification process, have yielded approximately 300 mg of the purified Fn14-TRAIL which was used for a series of in-vitro and in-vivo experiments indicated below.

EAE Experiments, with Human Fn14-Trail—Experimental Procedures

EAE was induced in 8-week-old female C57BL/6 mice by injecting subcutaneously, into the left para-lumbar region, 125 □g of myelin oligodendrocyte glycoprotein 35-55 (MOG 35-55) peptide (synthesized by Sigma Laboratories, Israel), emulsified in complete Freund's adjuvant (CFA) containing 5 mg/ml heat-killed *Mycobacterium tuberculosis*. Immediately thereafter, and, again, at 48 hours, the mice were inoculated with 300 ng of pertussis toxin. An additional injection of MOG 35-55 peptide in CFA was delivered 7 days later into the right para-lumbar region. From day 0 to day 8 mice were injected subcutaneously with 50, 100 or 200 micrograms a day of Fn14-Trail, or vehicle, in two equal doses (n=4 in each group). On day 9 the mice were treated for the last time, and sacrificed an hour later. Spleens were harvested and weighed. Pooled lymph node cells (LNCs) were prepared from inguinal, axillary and mesenteric lymph nodes or from spleens of mice that had been inoculated 9 days earlier with $MOG_{35}$-55 peptide in CFA with or without Fn14-TRAIL treatment. The ex vivo response of the lymphocytes was assayed in triplicate wells of 96-well flat-bottom plates. A total of $2\times10^5$ cells, suspended in 0.2 ml RPMI supplemented with 1% penicillin streptomycin, 1% glutamine and 5% fetal calf serum (FCS) and beta-mercapto-ethanol were added to each well. After 48 hrs, 1 µCi $^3$(H)Thymidine (Amersham, UK) was added to each well and the plates were incubated for an additional 18 hrs. Plates were then harvested with a semi-automatic harvester onto a glass fiber filter and the radioactivity was determined by liquid scintillation. The results are expressed as Stimulation Index (SI) according to the equation: SI=Mean cpm of the stimulated cells/mean cpm of the unstimulated cells.

Pooled spleen lymphocytes were isolated, using a Ficoll-Hipaque gradient, on day 9 from MOG-immunized mice treated with Fn14-Trail (n=4 animals in each group). Recovered cells were stained with methylene blue and counted. Mean number of lymphocytes per spleen in each group is presented.

The data from two duplicate experiments (FIGS. 12A and 12B) showed a significant dose-dependent decrease in splenocyte numbers, in the 50 ug to 200 ug range.

Pooled lymphocytes isolated from lymph nodes recovered on day 9 of Fn14-Trail treatment in MOG-immunized mice (n=4 in each group) were stimulated for 72 hrs with MOG peptide. Cultures were pulsed with [$^3$H]-thymidine 18 hrs before the end of incubation. Proliferation was estimated by [$^3$H]thymidine incorporation and was expressed as stimulation index (mean cpm of stimulated cells/mean cpm of non-stimulated cells. SI>2 represents significant stimulation).

The data (shown in FIG. 13) show significant Fn14-Trail-mediated inhibition of the recall response to MOG peptide rechallenge, with maximal effect obtained for mice treated with 100 µg/day/mouse.

EAE was induced by MOG challenge, as described above. On day 10 after MOG administration, mice (10 in each group) were treated with either vehicle or Fn14-Trail at 25, 50 and 100 µg/day, in two divided doses. Mice were followed daily for the evaluation of their clinical disease scores. The clinical status of mice was graded as follows: 0, no signs of disease; 1, tail weakness; 2, hind limb weakness sufficient to impair righting; 3, hind limb paresis; 4, paraplegia with forelimb weakness; 5, quadriplegia, 6, death. Treatment was stopped on day 26 after disease induction (day 16 of Fn14-Trail treatment). A: Mean clinical score of all experimental groups; B: Mean clinical score of the control group and the 100 µg/d group, in this case showing the S.D.

The data (shown in FIGS. 14A-14B) show a significant therapeutic effect of Fn14-Trail in reducing the progression of EAE disease, with a clear threshold dosing effect.

Collagen-Induced Arthritis, with Fn14-Trail—Experimental Procedures

DBA1 male mice were challenged twice (3 weeks apart) with 200 □g of type II collagen purified from bovine articular cartilage and emulsified in complete Freund's adjuvant (CFA: Difco Labs), via intradermal injection at the base of the tail. Mice were followed daily and monitored for swelling and/or erythema in one or more limbs. On the day of disease onset, mice were randomized for control group (treated with vehicle only) and treatment groups (one daily dose of 100 or 200 □g/mice/d of Fn14-Trail). Both vehicle and Fn14-Trail were administered subcutaneously. Injections were given daily for 14 days to the control and 100 ug group, and for 7 days to the 200 ug group. Mice were followed daily for 14 days from disease onset, and then every 3 days. Swelling in all 4 limbs was measured using a microcaliper, and compared to healthy, age-matched mice. The delta of swelling in each limb was calculated, and these deltas were summed into a score (disease index).

The data (shown in FIG. 15) show a significant therapeutic effect for Fn14-Trail treatment at the 200 ug/day dose. Of special note, the reduction in disease index persists for at least 7 days after cessation of Fn14-Trail treatment.

The Human Fn14-TRAIL Protein Induces Cancer Cell Death Via Apoptosis

Figure 16C:
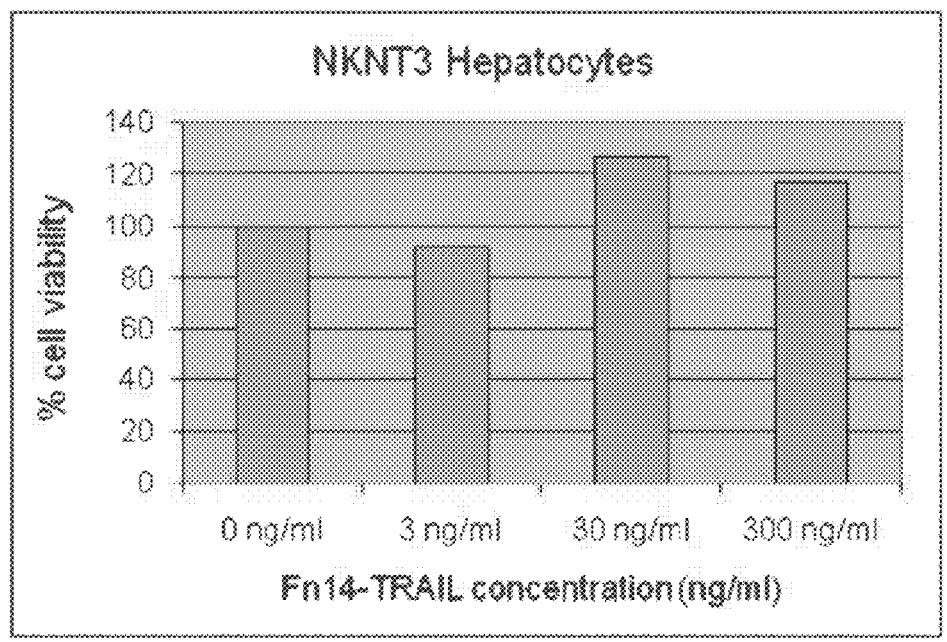
Figure 16D:
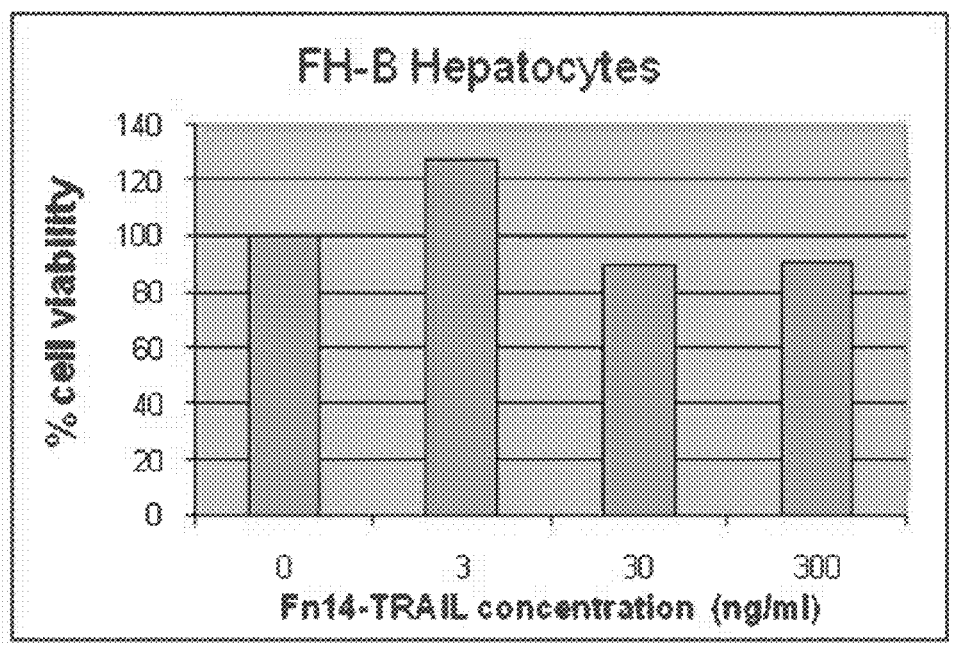

Fn14-TRAIL-Driven Cytotoxicity Against Cancer Cells is Highly Efficient and Specific Tumor cell cytotoxicity mediated by purified untagged human Fn14-TRAIL protein was studied with several human tumor cell types. The human hepatoma cancer cell-line SK-Hep1, which is known to be TWEAK-dependent and to express TRAIL receptors (DR5), was shown to be highly sensitive to Fn14-TRAIL, with the killing effect on this tumor line being extremely high (EC50=0.04 nM) (FIG. 16A). Similar efficacy was documented for two other hepatic tumor cell lines, Huh 7 and Hep-G2 (data not shown). In contrast to the effect on these hepatic tumor lines, incubation of Fn14-TRAIL at identical concentrations with non-cancer or non-hepatic cell lines showed no killing effect. For example Fn14-TRAIL has exhibited no killing effect on the human malignant B cell line Raji, which lacks surface TRAIL receptors (FIG. 16B), nor on the non-malignant human hepatic cell line NKNT3, which does expresses the TRAIL receptor DR5 (FIG. 16C) and the human fetal hepatocyte cell line FH-B (FIG. 16D). These results establish that Fn14-TRAIL kills cancer cells efficiently and specifically.

Fn14-TRAIL's Tumoricidal Activity Cannot be Achieved by Simply Delivering its Component Parts in Combination The tumoricidal effect of the Fn14-TRAIL fusion protein was compared to the effect of its component parts added in combination. To this end, cell viability of the hepatoma cancer cell line SK-Hep1 was measured following incubation with either purified Fn14-TRAIL, soluble extracellular domain of TRAIL (sTRAIL) alone, soluble Fn14 fused to the Fc domain of IgG1 (Fn14-Fc), or the combination of both (Fn14-Fc+sTRAIL), at similar molar concentrations. Fn14-Fc displayed no tumoricidal activity against this cancer cell line, while sTRAIL showed some killing effect. However, even the combination of both Fn14-Fc and sTRAIL did not achieve the tumoricidal effect of the fusion protein (FIG. 17).

Fn14-TRAIL Kills Cancer Cells by Inducing Apoptosis

To mechanistically probe the killing effect of Fn14-TRAIL, cells of the human hepatoma cancer cell line SK-Hep 1 were incubated with increasing concentrations of purified Fn14-TRAIL, soluble Fn14 fused to the Fc domain of IgG (Fn14-Fc) alone, the soluble extracellular domain of TRAIL (sTRAIL) alone, or a combination of both (Fn14-Fc+sTRAIL). Following incubation with the respective proteins, the treated cells were analyzed by FACS to determine the percentage of cells undergoing apoptosis (FIG. 18), as assessed by annexin V/PI staining. This analysis indicated that the killing effect of Fn14-TRAIL is apoptosis-based. Of note, soluble TRAIL (sTRAIL) alone demonstrated pro-apoptotic activity, but only at the highest concentration, with dramatic advantage for the fusion protein over the components alone or in combination at the 30 ng/ml concentration.

Whereas particular embodiments of this invention have been described above for purposes of illustration, it will be evident to those skilled in the art that numerous variations of the details of the present invention may be made without departing from the invention as defined in the appended claims.

What is claimed is:

1. A fusion protein comprising a first domain and a second domain, wherein the first domain is a polypeptide that binds to TWEAK and the second domain is a polypeptide that binds to a TRAIL receptor, wherein the first domain is at least a portion of the extracellular domain of Fn14 protein and the second domain is at least a portion of the extracellular domain of a TRAIL protein.

2. A fusion protein comprising a first domain and a second domain, wherein the first domain is a polypeptide that binds to TWEAK and the second domain is a polypeptide that binds to a TRAIL receptor, wherein the fusion protein is SEQ. ID. NO: 1 or SEQ. ID. NO: 2.

3. A fusion protein consisting of a first domain and a second domain, wherein the first domain is at least a TWEAK-binding portion of the extracellular domain of Fn14 protein and the second domain is at least a TRAIL receptor-binding portion of the extracellular domain of TRAIL protein.

4. A fusion protein comprising a first domain and a second domain, wherein the first domain is human Fn14 and the second domain is human TRAIL.

5. A pharmaceutical composition comprising the fusion protein of claim 1 and a pharmaceutically acceptable carrier.

6. A method of inhibiting inflammation in a patient having autoimmune disease comprising administering an effective amount of the pharmaceutical composition of claim 5.

7. The method of claim 6, wherein the autoimmune disease is multiple sclerosis.

8. The method of claim 6, wherein administration is parenteral.

9. The method of claim 6 wherein the patient has an alloimmune disease.

* * * * *